United States Patent [19]

Chu et al.

[11] Patent Number: 5,558,834
[45] Date of Patent: Sep. 24, 1996

[54] DEVICE AND METHOD OF SEPERATING AND ASSAYING WHOLE BLOOD

[75] Inventors: Amy H. Chu, Granger; Lon R. Stover, Elkhart, both of Ind.

[73] Assignee: Bayer Corporation, Elkhart, Ind.

[21] Appl. No.: 454,614

[22] Filed: May 31, 1995

Related U.S. Application Data

[63] Continuation of Ser. No. 218,149, Mar. 25, 1994, abandoned, which is a continuation of Ser. No. 770,467, Oct. 3, 1991, abandoned.

[51] Int. Cl.$^6$ .................................................. G01N 33/48
[52] U.S. Cl. ................... 422/55; 436/66; 436/518; 436/524; 436/810; 436/169; 422/57; 422/58; 422/61; 422/73; 422/69; 210/496; 427/2.13; 435/13
[58] Field of Search ................... 422/55–58, 61, 422/68.1, 69, 73; 435/7.1, 13, 14; 436/5, 16, 45, 63, 66, 169, 177, 178, 526, 531, 501, 518, 524, 810; 210/483, 488, 496, 504, 506; 427/2.13, 244

[56] References Cited

U.S. PATENT DOCUMENTS

| | | | |
|---|---|---|---|
| 3,092,465 | 6/1963 | Adams et al. | 435/28 |
| 3,298,789 | 1/1967 | Mast | 435/26 |
| 3,552,925 | 7/1967 | Fetter | 422/56 |
| 3,552,928 | 1/1971 | Fetter | 422/56 |
| 3,607,093 | 9/1971 | Stone | 422/56 |
| 3,884,896 | 5/1975 | Blomback et al. | 435/13 |
| 4,057,394 | 11/1977 | Grenshaw | 422/56 |
| 4,059,405 | 8/1976 | Sodickson et al. | 422/67 |
| 4,144,306 | 3/1979 | Figueras | 422/56 |

(List continued on next page.)

FOREIGN PATENT DOCUMENTS

| | | |
|---|---|---|
| 0143574 | 6/1985 | European Pat. Off. . |
| 0295526 | 12/1988 | European Pat. Off. . |
| 0436897 | 12/1990 | European Pat. Off. . |
| 0415679 | 3/1991 | European Pat. Off. . |
| 3441149 | 5/1986 | Germany . |
| 3508427 | 9/1986 | Germany . |
| 8702267 | 4/1987 | WIPO . |

OTHER PUBLICATIONS

Exhibit 1, nonhemolytic surfactants which have a different names.
G. Rayman and J. L. Day, The Lancet, Nov. 12, 1988 "New Device to Improve the Accuracy of Bedside Blood Glucose Test", pp. 1107–1109.

*Primary Examiner*—Jill Warden
*Assistant Examiner*—Harold Y. Pyon
*Attorney, Agent, or Firm*—Roger N. Coe; Roger N. Coe

[57] ABSTRACT

An improved device and method of separating the cellular components of whole blood from plasma or serum and assaying the plasma or serum for a predetermined soluble constituent are disclosed. The device includes a filter pad, that separates the cellular components of whole blood from the serum or plasma, and a test pad, that assays the serum or plasma for a predetermined soluble constituent. The filter pad effectively separates and retains cellular components of the whole blood sample, thereby eliminating assay interference by the cellular components of whole blood. The method includes contacting the whole blood with a test device including a filter pad comprising a suitable carrier matrix homogeneously incorporating therein a separating reagent composition comprising a) separating reagent, like an agglutinin, such as a blood type nonspecific lectin; a coagulant, such as a thrombin or a thrombin-like compound; or a mixture thereof, and b) a nonhemolytic surfactant, like an ethoxylated or propoxylated nonionic or anionic surfactant, such that the cellular components of the whole blood are separated from the plasma or serum as the blood permeates through the filter pad, The essentially cell-free plasma or serum then saturates a test pad that is in contact with the filter pad. After the plasma or serum saturates the test pad, the test pad is examined for a qualitative or quantitative response to a predetermined soluble constituent of the whole blood.

16 Claims, 4 Drawing Sheets

U.S. PATENT DOCUMENTS

| | | | |
|---|---|---|---|
| 4,157,323 | 6/1979 | Yen et al. | 436/526 X |
| 4,186,251 | 1/1980 | Tarbutton | 435/11 |
| 4,258,001 | 3/1981 | Pierce et al. | 422/56 |
| 4,301,027 | 11/1981 | Blümcke et al. | 422/55 |
| 4,436,823 | 3/1984 | Blümcke et al. | 436/169 |
| 4,477,575 | 10/1984 | Vogel et al. | 436/170 |
| 4,604,264 | 8/1986 | Rothe et al. | 422/56 |
| 4,613,567 | 9/1986 | Yasoshima et al. | 435/7 |
| 4,649,123 | 3/1987 | Charlton et al. | 422/56 |
| 4,656,252 | 4/1987 | Giese | 435/6 |
| 4,678,757 | 7/1987 | Rapkin et al. | 436/169 |
| 4,774,192 | 9/1988 | Terminiello et al. | 436/530 |
| 4,816,224 | 3/1989 | Vogel et al. | 422/55 |
| 4,839,296 | 6/1989 | Kennedy et al. | 436/170 |
| 4,844,966 | 7/1989 | Calenoff et al. | 435/7 |
| 4,886,761 | 12/1989 | Gustafson et al. | 436/518 |
| 4,933,092 | 6/1990 | Aunet et al. | 210/729 |
| 4,959,307 | 9/1990 | Olson | 435/7 |
| 4,975,217 | 12/1990 | Brown-Skrobort et al. | 252/107 |
| 4,987,085 | 1/1991 | Allen et al. | 436/169 |
| 5,064,541 | 11/1991 | Jeng et al. | 436/177 |
| 5,077,011 | 12/1991 | Amano et al. | 422/56 |
| 5,085,987 | 2/1992 | Olson | 435/7.91 |
| 5,085,988 | 2/1992 | Olson | 435/7.91 |
| 5,130,231 | 7/1992 | Kennedy et al. | 422/56 |
| 5,147,771 | 9/1992 | Sutton et al. | 435/5 |

DEVICE AND METHOD OF SEPERATING AND ASSAYING WHOLE BLOOD

This is a continuation of U.S. application Ser. No. 08/218,149, filed Mar. 25, 1994, now abandoned, which is a continuation of U.S. application Ser. No. 07/770,467, filed Oct. 3, 1991, now abandoned.

FIELD OF THE INVENTION

The present invention relates to an improved device and method of separating the cellular components of whole blood from the plasma or serum, and assaying the plasma or serum for a predetermined soluble constituent. More particularly, the present invention relates to an improved method of removing cellular components from whole blood by utilizing a filter pad comprising a suitable carrier matrix homogeneously incorporating therein a separating reagent composition comprising a separating reagent, like an agglutinin, such as a lectin; a coagulant, such as a thrombin or a thrombin-like compound; or a combination thereof, and a nonhemolytic surfactant, like an ethoxylated or propoxylated nonionic or anionic surfactant. The essentially cell-free plasma or serum, in an undiluted and unaltered form, then saturates a reagent-impregnated test pad that is in contact with the filter pad. After the undiluted plasma or serum saturates the test pad, the test pad then is examined for a response, such as a color change, to provide a prompt and accurate qualitative or quantitative assay for one or more soluble constituents of the plasma or serum. In one embodiment, the filter pad, contaminated with the cellular components of the whole blood, is separated from contact with the test pad, and the exposed surface of the test pad is examined for a response. In another embodiment, the filter pad and the test pad remain in contact, and a surface of the test pad free from contact with the filter pad is examined for a response.

BACKGROUND OF THE INVENTION

Presently, numerous test devices are available to simply and rapidly analyze body fluids for the presence or absence of a predetermined soluble constituent. For example, tests are available to detect glucose, uric acid or protein in urine, or to detect glucose, triglycerides, potassium ion or cholesterol in blood. Historically, assays of a whole blood sample for a predetermined soluble constituent are the most difficult tests to design.

The cellular components of whole blood, and especially the red blood cells, are the primary interfering substances in assays for a soluble constituent of whole blood. Most simple blood tests are chromogenic, whereby a predetermined soluble constituent of the whole blood interacts with a particular reagent either to form a uniquely-colored compound as a qualitative indication of the presence of absence of the constituent, or to form a colored compound of variable color intensity as a quantitative indication of the presence of the constituent. The deep red color of the whole blood sample substantially interferes with these chromogenic tests, and therefore the highly-colored red blood cells usually are separated from the plasma or serum before the blood sample is assayed for a predetermined soluble constituent.

The presence of red blood cells also can interfere with various nonchromogenic blood assays, whereby the assay results are either inconsistent or, if consistent, are inaccurate. Furthermore, other cellular components, including the white blood cells, also can interfere in standard chromogenic blood assays. Therefore, to achieve a reliable assay for a predetermined soluble constituent of whole blood, it is essential to separate the serum or plasma from the cellular components of whole blood prior to analyzing the whole blood sample for the predetermined soluble constituent.

Conventionally, the plasma or serum is separated from the cellular material of whole blood by centrifugation. The cellular material collects at the bottom of the centrifuge tube and the supernatant plasma or serum is decanted. Accordingly, the interfering cellular components of whole blood are sufficiently removed such that a substantial background interference is avoided. However, the centrifuge method has the major disadvantages of requiring a relatively large blood sample, usually from about 0.1 ml to about 5 ml, and a long centrifuge time of approximately 5 to 10 minutes. Furthermore, the centrifuge method requires several manipulative steps. Consequently, a laboratory technician may contact a potentially-infectious blood sample or contact laboratory equipment contaminated by the relatively large blood sample.

Overall, the centrifuge method is best suited for large, automated laboratories that assay a large number of blood samples, and for institutions, such as hospitals, that do not require assay results in a matter of minutes. Many small laboratories and private medical offices do not have a centrifuge or other blood separator on site. Therefore, simple chromogenic tests cannot be performed quickly, safely and easily on site and the whole blood sample is sent to an outside laboratory for efficient and safe separation and assay. As a result, the assay results are available in hours or days as opposed to minutes.

Accordingly, investigators have continually sought a device and method of quickly, safely and easily separating essentially all of the interfering cellular components of whole blood from the plasma or serum such that the identity and concentration of soluble constituents in the plasma or serum are not altered. Consequently, an assay for a predetermined constituent of the plasma or serum is trustworthy, accurate and free from interference by the cellular components of the whole blood. Investigators have provided several methods and devices for separating the interfering cellular components of whole blood from the plasma or serum. However, each method and device possessed at least one disadvantage that made the method or device inaccurate, cumbersome of impractical in assaying a whole blood sample for a predetermined soluble constituent.

Methods other than centrifugation have been used to separate the cellular components of a small whole blood sample from the serum or plasma. One of the simpler methods, as disclosed by Adams et al. in U.S. Pat. No. 3,092,465, used a bibulous, or moisture absorbing, matrix that is impregnated with a chromogenic testing reagent and coated with a semipermeable barrier. The semipermeable barrier screens the cellular components of the whole blood sample and permits passage of the smaller, soluble molecules and ions to contact the chromogenic testing reagent incorporated into the bibulous matrix. In the case of a positive test, the essentially colorless plasma or serum interacts with the chromogenic testing reagent to produce a color in the bibulous matrix. The color is observed by rinsing or wiping the cellular material retained on the semipermeable barrier from the test device. However, the rinsing of wiping technique is cumbersome and laborious, and assay interference is possible if the red blood cells are not completely wiped or rinsed from the semipermeable barrier. In addition, the possibility of technician contact with the potentially-infectious blood sample is high. Mast, in U.S. Pat. No. 3,298,789, discloses a similar device, wherein a film of ethylcellulose is utilized as the semipermeable barrier. Sodickson, in U.S. Pat. No. 4,059,405, discloses separation of the cellular components from the blood plasma or serum with an ultrafiltration membrane.

Fetter in U.S. Pat. Nos. 3,552,925 and 3,552,928 discloses another method and device to assay small whole blood samples for soluble constituents. Fetter describes a test device having a bibulous matrix impregnated with a nonvolatile inorganic salt or an amino acid at a first region on the matrix and impregnated with a test reagent at an adjacent second region of the matrix. A whole blood sample is introduced onto the bibulous matrix such that the whole blood first contacts the first region of the bibulous matrix including the inorganic salt or amino acid. The salt or amino acid precipitates the cellular components from the blood, and the plasma or serum then migrates to the test reagent-impregnated second region of the bibulous matrix for a chromogenic interaction with the test reagent. The salts or amino acids used in this process effectively separate the red blood cells from the whole blood sample, but also introduce contaminating ions or molecules into the plasma or serum and precipitate a portion of the soluble plasma or serum constituents. Therefore, the method of Fetter may suffer from the disadvantage that a quantitative assay for a predetermined soluble constituent of the plasma or serum is unreliable because the plasma or serum no longer includes the true concentration of the predetermined soluble constituent, or constituents, of interest.

Another prior art method of separating the cellular components of whole blood from the plasma or serum was disclosed by Vogel et al., U.S. Pat. No. 4,477,575, describing a process and a composition for separating plasma or serum from whole blood using a layer of glass fibers having a defined average diameter and density. In addition to the defined glass fiber parameters, the amount of plasma or serum that can be separated is limited to at most 50%, and preferably less than 30%, of the absorption volume of the glass fibers. Otherwise, whole blood, containing approximately 50% filterable cellular material, effectively clogs the glass fiber layer. Therefore, the method requires a high ratio of glass fibers to whole blood volume. Vogel et al. do not teach or suggest including an agglutinin, a thrombin or a thrombin-like compound, or a nonhemolytic surfactant, in the layer of glass fibers.

In other prior art methods, the whole blood is diluted before assaying for a predetermined soluble plasma or serum constituent. The dilution of whole blood is burdensome because an extra manipulative step is required, and dilution introduces the possibility of assay error because of an incorrect dilution of the blood sample. The possibility of technician contact with the potentially infectious blood sample also is increased. For example, German Patent Publication No. DE-OS 34 41 149 discloses a method of separating plasma or serum from whole blood by passing the whole blood through a lectin-impregnated matrix that is repeatedly rinsed with a diluent to dilute the plasma or serum before the assay is performed. The agglutinating ability of the lectin was enhanced by including a cationic polymer in the matrix. However, the possibility of imprecise dilution can result in an inaccurate assay for the plasma or serum constituent of interest. German Patent Publication No. DE-OS 34 41 149 neither teaches nor suggests that a nonhemolytic surfactant can enhance the ability of a lectin to agglutinate cellular material. The use of a lectin or a polymeric amino acid to separate the cellular material from a whole blood sample is also disclosed in European Patent Application No. 84307633.2.

In developing a method and device for separating and assaying small whole blood samples, a primary consideration is the degree of sophistication of the technician performing the assay. Often it is desirable to have relatively untrained personnel perform routine assays and obtain accurate quantitative results. Therefore, it is important that the assay method include a minimum of manipulative steps, be free of possible interferences or contamination, minimize or eliminate the possibility of laboratory personnel physically contacting the blood sample, and provide for easy measurement. For instance, among the several possible manipulative steps, the dilution of the whole blood, or the plasma or serum, prior to the actual assay introduces the most probable step for assay error or personal contact with the blood sample. Another common manipulative error is the incomplete wiping or rinsing of the cellular components of whole blood from the surface of a device that utilizes a cell-impermeable membrane to separate the cellular components from the plasma or serum of whole blood.

Therefore, a need exists for a method and device to efficiently separate and accurately assay small volumes of whole blood. The method preferably avoids a distinct manipulative step to separate the cellular components from the plasma or serum prior to the assay. Furthermore, in order to avoid dilution errors, the method preferably allows the assay of undiluted plasma or serum. It also is desirable to provide a blood separation and blood assay method that protects the technician from contact with the blood sample; that avoids the time delays of the present methods; and that yields accurate and reproducible results.

The ideal method includes withdrawing a whole blood sample in a "noninvasive" amount, such as a pin prick drop, and immediately depositing the undiluted whole blood sample on a test device that both separates the cellular components from the undiluted plasma or serum, and assays the undiluted plasma or serum for the presence or concentration of a predetermined soluble constituent within minutes. Alternatively, the test device can contact a finger puncture and withdraw a fresh, undiluted blood sample from the wound for analysis. Such a separation and assay method and device allow medical personnel to perform whole blood analyses on a more routine and more confident basis.

Consequently, investigators have attempted to develop test devices that include an element to separate, collect and retain the cellular components of whole blood. In addition, some test devices were developed wherein the cell-separating element then is physically disconnected from the test device and discarded before assaying the plasma or serum for a particular constituent. For example, the previously-mentioned Vogel et al. U.S. Pat. No. 4,477,575 discloses a device wherein a glass fiber cell-separating layer is disposed over a reaction layer, such that the separating layer can be removed from the reaction layer. The reaction layer then is examined for response to a particular plasma or serum constituent. However, the glass fiber separating layer of the Vogel device requires the disadvantageous high ratio of glass fiber to blood described above. Consequently, a specific volume of blood must be pipetted onto the test device, thereby adding a time-consuming manipulative step that can result in operator error and erroneous assays. Such a manipulative step also can lead to reduced operator safety because of potential physical contact between the operator and the blood sample.

Rothe et al., in U.S. Pat. No. 4,604,264, discloses a hinged assay device. The device disclosed by Rothe et al. includes a separating layer consisting of a glass fiber fleece, wherein the whole blood is applied near the end of the separating layer distant from the hinge area of the device. The separating layer includes neither an agglutinin, like a lectin, nor a coagulant, like a thrombin or a thrombin-like compound, nor a nonhemolytic surfactant. As the blood permeates through the separating layer, the cellular components are separated from the serum or plasma. The serum or plasma then migrates towards the hinge of the device to an area of the separating layer underneath a reaction/indicator layer that is disposed above the separating layer and secured to the separating layer by a hinge. By pressing down on the reaction/indicator layer, contact between the lower face of the reaction/indicator layer and the separating layer allows the reaction/indicator layer to absorb the serum or plasma for reaction with reagents in the reaction/indicator layer. Assay detection, such as a color change, is achieved by observation through a transparent film disposed on the upper face of the reaction/indicator layer.

Kennedy et al., in application PCT/US86/02192, disclose a disposable dry phase test stick having a reactive area covered by a semipermeable membrane. The semipermeable membrane separates cellular and particulate matter from whole blood and allows the plasma or serum to contact the reactive area. The semipermeable membrane is detachable from the reactive area to remove cellular components and particulate matter from the device and to expose the reactive area for examination of a response to a particular analyte. The semipermeable membrane is a hydrophobic polytetrafluoroethylene material rendered hydrophilic with a surfactant or a soap-like wetting agent. Kennedy et al. disclose that the surfactant, either a nonionic surfactant, anionic surfactant, or cationic surfactant, is included to make the semipermeable membrane hydrophilic and to distribute blood sample so that the blood sample spreads rapidly and evenly through the semipermeable membrane. However, Kennedy et al. do not teach or suggest that a surfactant improves the ability of a small amount of an agglutinin or a coagulant to separate the cellular components from a test sample. In contrast to the present invention, wherein an agglutinin or a coagulant is utilized in a low amount, and in conjunction with a nonhemolytic surfactant, to separate the cellular material, Kennedy et al. teach the separation of the cellular material by a hydrophobic semipermeable membrane, absent an agglutinin or a coagulant, made hydrophilic with a surfactant. Furthermore, the cationic and anionic wetting agents disclosed by Kennedy et al. can remove particular noncellular components, such as potassium ions, from the plasma or serum.

Another prior art patent directed to separating the cellular components of whole blood from the plasma or serum is Rapkin et al. U.S. Pat. No. 4,678,757, wherein a carbohydrate-treated permeable carrier is used to separate the cellular components of whole blood from the plasma or serum. The plasma or serum of the whole blood then contacts a reagent-treated permeable carrier for assay of a particular blood constituent. In this device, the cellular components collect and are retained at the bottom edge of the carbohydrate-tested carrier, and the plasma or serum permeates through the carbohydrate-treated carrier to contact the reagents necessary for the assay. Assay results are determined by observation through a transparent material covering the permeable layers. Rapkin et al. disclose that sugars, like mannitol, sucrose, glucose and sorbitol, are suitable carbohydrates. Rapkin et al. do not teach incorporating a nonhemolytic surfactant, or an agglutinin or a coagulant, in the carbohydrate-treated permeable carrier.

In addition, Terminiello et al., in U.S. Pat. No. 4,774,192, disclose a porous membrane having a porosity gradient such that the cellular components of whole blood are retained in an area of the membrane having a low porosity. The porous membrane is conditioned with a protein, a sugar, a polyethylene glycol, a polypyrolidone or similar compound to reduce the void space within the matrix membrane (i.e., to lower the porosity of the membrane) and to promote absorption of the fluid portion of the test sample. Therefore, the serum or plasma can flow through the area of low porosity to contact assay reagent components incorporated into an area of the membrane having a high porosity. G. Rayman and J. L. Day, in the publication "New Device to Improve the Accuracy of Bedside Blood Glucose Tests", *The Lancet*, Nov. 12, 1988, pp. 1107–1109, describe a disposable test strip for glucose wherein the surface of the strip is wiped to remove the cellular components of the whole blood from the strip. However, in the Terminiello et al. device, higher molecular weight soluble plasma components, such as cholesterol, may not completely permeate through the low porosity area of the membrane; and in the Rayman and Day device the cellular components may not be completely wiped from the surface of the strip. Therefore, in each device, inaccurate and unreliable assays are possible. Neither disclosure suggests that a nonhemolytic surfactant can be included in a separating layer such that the amount of agglutinin or coagulant in the separating layer can be reduced substantially. Other patents directed to assaying whole blood for a predetermined soluble constituent wherein the cellular components are separated from the plasma include: Stone, U.S. Pat. No. 3,607,093; Figueras, U.S. Pat. No. 4,144,306; and Pierce et al., U.S. Pat. No. 4,258,001.

Therefore, because of the disadvantages present in the above-cited methods and test devices, it is apparent that a simple and effective method of separating the cellular components of whole blood to provide essentially cell-free, unaltered and undiluted plasma or serum is needed. Accordingly, the method and device of the present invention allow the safe, accurate and economical assay of a whole blood sample, or other biological fluid sample, for a predetermined soluble constituent by utilizing a filter pad having incorporated therein: a) a separating reagent, such as an agglutinin, like a blood type non-specific lectin; a coagulant, like a thrombin or a thrombin-like compound; or a combination thereof; and b) a nonhemolytic surfactant, like an ethoxylated or propoxylated nonionic or anionic surfactant, to achieve essentially complete separation of the cellular components of whole blood from the plasma or serum. The filter pad is in contact with a test pad incorporating the necessary reagents to assay for the predetermined plasma or serum constituent of interest. The essentially cell-free plasma or serum migrates through the filter pad to contact the test pad. An interaction between the predetermined constituent of interest and the assay reagents produces a detectable response, such as a color transition, free from interferences attributed to highly-colored cellular components.

The method and device of the present invention allow the assay of whole blood without resorting to lengthy and expensive wet phase assays and without resorting to the extra manipulative step of diluting the test sample. The cell-free plasma or serum that saturates the test pad is unaltered and undiluted, thereby allowing a more accurate and trustworthy assay for a predetermined soluble constituent. The method and device of the present invention also eliminate the disadvantages of hematocrit sensitivity, technique sensitivity due to wiping or rinsing the cellular components from the test device, and disposal of the cellular components.

Furthermore, in accordance with one embodiment of the present invention, after the whole blood sample has saturated the filter pad and the test pad, the filter pad retaining the cellular components of the blood can be physically disconnected from the test device, and thereby exposing the test pad of the device. The test pad, saturated with undiluted and unaltered plasma or serum, then is examined for a response to a predetermined plasma or serum constituent by standard dry phase chemistry test strip procedures. Alternatively, in another embodiment, the filter pad is not removed from the test device, and a surface of the test pad free from contact with the filter pad is examined for a response, such as examination through a transparent support.

In accordance with another important feature of the present invention, the device essentially precludes contact between the technician and the blood sample. The blood sample is absorbed into the filter pad in such a manner that excess blood sample does not remain on an outside surface of the device. In addition, the technician need not wipe or rinse the cellular components from the device before examination of the device for a response. Consequently, the device essentially eliminates the possibility of contact between the technician and a potentially infectious blood sample.

As a result of the present invention, the assay of plasma or serum for a predetermined soluble constituent is accurate and reliable because the interferences attributed to the highly-colored cellular components are essentially eliminated. Prior methods and devices rely either upon wiping the cellular components from the surface of the analyte detection device or upon immobilizing the cellular components, physically or chemically, in an area of the analyte detection device distant from the actual assay area. As will be demonstrated more fully hereinafter, the device of the present invention provides an accurate and economical method of first separating the cellular components of whole blood from the plasma or serum by an improved filter pad.

Unexpectedly, it has been found that the filter pad utilized in the present invention effectively separates the cellular components from a whole blood sample by incorporating a relatively small amount of an agglutinin, like a lectin; a coagulant like a thrombin or a thrombin-like compound, or a combination thereof, in the filter pad. Surprisingly, only a relatively small amount of agglutinin or coagulant is incorporated into the filter pad because a nonhemolytic surfactant also is incorporated into the filter pad. Furthermore, the serum or plasma is distributed evenly throughout the entire test pad, therefore the assay response is homogeneous throughout the test area of the device.

U.S. patent application Ser. No. 063,680, filing date Jun. 19, 1987, and commonly assigned to the assignee of the present invention, discloses that an agglutinin or a coagulant included in a filter pad effectively separates the interfering cellular material from a whole blood sample. However, the filter pad was impregnated with a relatively large amount of expensive agglutinin or coagulant to achieve a satisfactory separation. In addition, because the purity or activity of an agglutinin or coagulant can vary, including a large amount of agglutinin or coagulant in a filter pad can lead to clogging of the filter resulting in inconsistent or irreproducible results. Therefore, in accordance with an important feature of the present invention, it has been found that incorporating a nonhemolytic surfactant into the filter pad allows a significant reduction in the amount of agglutinin or coagulant incorporated in the filter pad. Consequently, the filter pad and test device of the present invention are more economical, separate essentially all of the cellular components from a whole blood sample, and provide more consistent and reproducible assays.

SUMMARY OF THE INVENTION

In brief, the present invention is directed to a device and method of separating the cellular components from whole blood and assaying the undiluted and unaltered serum or plasma for a predetermined soluble constituent, or constituents, without additional manipulative steps. It has been found that separating the cellular components of whole blood from the plasma or serum by the method and device of the present invention provides an essentially cell-free, undiluted and unaltered serum or plasma sample for assay of a predetermined soluble constituent. The separation method and device do not introduce contaminants into the serum or plasma, and do not alter the compositional makeup of the plasma or serum. Furthermore, the method and test device of the present invention also can be used to assay other biological fluids having cellular or particulate matter that interfere in an assay for a predetermined soluble constituent.

In accordance with an important feature of the present invention, the device includes a filter pad, that separates the cellular components of whole blood from the serum of plasma, in contact with a test pad that assays the undiluted and unaltered serum or plasma for a predetermined soluble constituent. The filter pad comprises a suitable carrier matrix incorporating a separating reagent composition to separate the cellular blood components from the serum of plasma. In accordance with the present invention, the filter pad effectively separates the cellular components from the whole blood sample, thereby precluding the cellular components from interfering with the assay for a soluble constituent of the blood or plasma and facilitating the assay of the serum or plasma for a predetermined constituent. The serum or plasma, in an undiluted and unaltered form, is assayed for a predetermined soluble constituent by the specific indicator reagent composition incorporated into the test pad. The method and device also essentially preclude technician contact with a potentially infectious blood or other biological sample.

In one embodiment of the present invention, the filter pad is detached from the device, and the exposed test pad is examined for a response, such as a color change, to a predetermined soluble constituent of the whole blood. In another embodiment, the filter pad and the test pad remain in contact, and a surface of the test pad free from contact with the filter pad is examined for a response. The present invention eliminates technique dependence from the assay, such as eliminating the manipulative step of wiping or rinsing the cellular components from the test device, and also assures that the proper volume of plasma or serum contacts the test pad of the device. Furthermore, technician contact with the potentially infectious blood or other biological sample is essentially precluded.

The method includes first contacting a whole blood sample with a test device comprising a filter pad, including a suitable carrier matrix incorporating a separating reagent composition, and a test pad, including a suitable substrate material incorporating an indicator reagent composition. As used here, and hereinafter, the expression "separating reagent composition" is defined as a chemical or mixture of chemicals that separates the cellular components of whole blood from the remaining soluble blood constituents. Likewise, as used here and hereinafter, the expression "indicator reagent composition" is defined as a chemical or mixture of chemicals causing a detectable interaction upon contact with the predetermined soluble constituent of interest. The whole blood sample initially contacts only the filter pad of the test device. The whole blood sample permeates through the filter pad wherein the red blood cells and other cellular and particulate components of the whole blood are separated from the plasma or serum through the action of the separating reagent composition and the carrier matrix. The undiluted and unaltered plasma or serum continues to permeate through the filter pad to contact a test pad that is in contact with the filter pad.

The assay of interest is performed by the test pad of the device. The undiluted plasma or serum interacts with the indicator reagent composition previously incorporated into the test pad to produce a detectable, and preferably a measurable, change in the test pad, such as a color change, to show the presence of a predetermined soluble constituent, or to permit a quantitative determination of a predetermined soluble constituent. The test pad then is examined, either visually or by instrument, for a qualitative or quantitative response to the predetermined soluble constituent of interest. After examination for a response, the test device is discarded. Consequently, the assay for the predetermined soluble constituent of interest is achieved by using a simple and inexpensive test device that effectively separates the interfering cellular and particulate components from the test sample without manipulative steps, such as wiping or rinsing, that can lead to technician error or technician contact with a potentially infectious blood sample.

Therefore, the present invention is directed to a method and device for rapidly and effectively separating the cellular components from the plasma or serum of undiluted whole blood and assaying the plasma or serum for a predetermined soluble constituent. More particularly, and in accordance with an important feature of the present invention, one or more filter pads are arranged to separate the cellular components from whole blood and to allow the plasma or serum to pass onto one or more test pads that are in contact with the filter pad, or pads. After a test pad is saturated with plasma or serum, the test pad is examined for a qualitative or quantitative response to a predetermined soluble serum or plasma constituent. Accordingly, assay interferences attributed to the cellular components of whole blood are eliminated, thereby achieving a more accurate and more reliable serum or plasma assay.

In accordance with an important feature of the present invention, a whole blood sample contacts a test device comprising a filter pad including a suitable carrier matrix incorporating therein a separating reagent composition comprising a separating reagent, such as an agglutinin, like a lectin; a coagulant, like thrombin or a thrombin-like compound; or a combination thereof, and a nonhemolytic surfactant. To achieve the full advantage of the present invention, the whole blood sample contacts a test device comprising a filter pad including a suitable carrier matrix incorporating a separating reagent composition comprising a lectin and a nonhemolytic surfactant. The filter pad achieves separation of the cellular components of the whole blood from the plasma or serum and does not add contaminating ions or molecules to, or remove soluble constituents from, the serum of plasma.

In accordance with another important feature of the present invention, the presence of a nonhemolytic surfactant in the filter pad allows the amount of agglutinin or coagulant present in the test pad to be reduced substantially, without adversely affecting the ability of the filter pad to separate the cellular components from the whole blood sample. It has been found that including from about 0.05% to about 3% by weight of a nonhemolytic surfactant in a separating reagent composition allows the amount of agglutinin of coagulant present in the separating reagent composition to be reduced by a factor of from about two to about five without adversely affecting the ability of the filter pad to separate the cellular components from the whole blood sample. Incorporating a separating reagent composition of the present invention into a suitable carrier matrix therefore provides an efficient and economical filter pad. Accordingly, the test strip is more economical and provides more reproducible results because less of the expensive and hard-to-reproduce separating reagent, i.e., agglutinin or coagulant, is included in the filter pad.

Therefore, the amount of agglutinin, like a lectin, included in the filter pad is in the range of from about 5 units to about 100 units, and preferably from about 5 units to 50 units, per $cm^3$ of carrier matrix material comprising the filter pad, wherein each "unit" is defined as the amount of lectin necessary to agglutinate a two percent solution of red blood cells within one hour of incubation at 25° C. The amount of coagulant, like thrombin or thrombin-like compound, such as acutase, agkistrodon contortrix, ancrod, atroxin and crotalase, or combinations thereof, included in the filter pad is in the range of from about 20 to about 200 NIH (National Institute of Health) units, and preferably from about 40 to about 100 NIH units, per $cm^3$ of carrier matrix material comprising the filter pad.

Therefore, the present invention is directed to a method and device for rapidly and effectively separating the cellular components from the plasma or serum on an undiluted whole blood sample. More particularly, and in accordance with another important feature of the present invention, a filter pad, incorporating a separating reagent composition, is arranged on a test strip so as first to separate the cellular components of whole blood from the serum or plasma, and then a test pad assays the serum or plasma, qualitatively or quantitatively, for a predetermined soluble constituent. The whole blood contacts a filter pad incorporating a separating reagent composition comprising a) a coagulant, like a thrombin or a thrombin-like compound or, preferably, an agglutinin, like a lectin; and b) a nonhemolytic surfactant. The filter pad separates the cellular components from the whole blood without adding contaminating ions or molecules to, or removing soluble constituents from, the serum or plasma. The undiluted serum or plasma passes through the filter pad of the device, essentially unimpeded, to saturate the test pad of the device, and the assay of interest is performed. The test pad of the device, comprising an indicator reagent composition homogeneously incorporated into a suitable substrate material, is in contact with the filter pad. In accordance with an important feature of the present invention, the predetermined plasma or serum constituent of interest is detected or measured without performing any additional manipulative steps, such as diluting the plasma or serum or wiping or rinsing the test device.

Therefore, an important aspect of the present invention is to provide a method and device to quickly and effectively separate the cellular and other particulate components from the plasma or serum of small whole blood samples or other biological samples. The method and device allow the rapid, easy and effective separation of undiluted and essentially unaltered plasma or serum from the cellular components of whole blood, such that the plasma or serum can be assayed for a predetermined soluble constituent without additional manipulative steps. Accordingly, interferences attributed to the cellular components of whole blood in assays of undiluted and unaltered plasma or serum for a predetermined soluble constituent are eliminated.

Another important aspect of the present invention is to provide a method of separating the cellular components from a whole blood sample by utilizing a separating reagent composition comprising a) an agglutinizing compound or a coagulating compound, or a combination thereof, as the separating reagent, and b) a nonhemolytic surfactant. The agglutinizing compound or coagulating compound is a lectin, a thrombin, a thrombin-like compound or a combination thereof, and is used in conjunction with a nonhemolytic surfactant.

A new and improved test device of the present invention assays, qualitatively or quantitatively, a small sample volume of whole blood to essentially eliminate assay interferences attributed to the cellular components of the whole blood sample. The test device for assaying an undiluted whole blood sample for a predetermined soluble constituent comprises a filter pad to remove the cellular components of the whole blood, and a test pad incorporating an indicator reagent composition in contact with the filter pad to assay the plasma or serum for the predetermined soluble constituent. The test pad of the dry phase test strip device comprises a substrate material capable of homogeneously incorporating an indicator reagent composition that interacts with the predetermined constituent of interest in the serum or plasma. The filter pad, in contact with the test pad, comprises a suitable carrier matrix having incorporated therein a separating reagent composition comprising a lectin, a thrombin or a thrombin-like compound and a nonhemolytic surfactant, that interacts with, and separates, the cellular components of the whole blood from the plasma or the serum. The new and improved test device and method assay for the presence or concentration of a predetermined constituent in whole blood, whereby a whole blood sample contacting the filter pad first is separated into cellular components and into undiluted plasma or serum. The cellular components remain in the filter pad and the undiluted plasma or serum permeates through the filter pad. Then, the undiluted plasma or serum contacts the test pad to produce a detectable or measurable response to the predetermined constituent of interest.

BRIEF DESCRIPTION OF THE DRAWINGS

The above and other aspects, advantages and novel features of the present invention will become apparent from the following detailed description of the preferred embodiments of the present invention taken in conjunction with the following figures wherein.

DETAILED DESCRIPTION OF THE INVENTION

Figure 1:
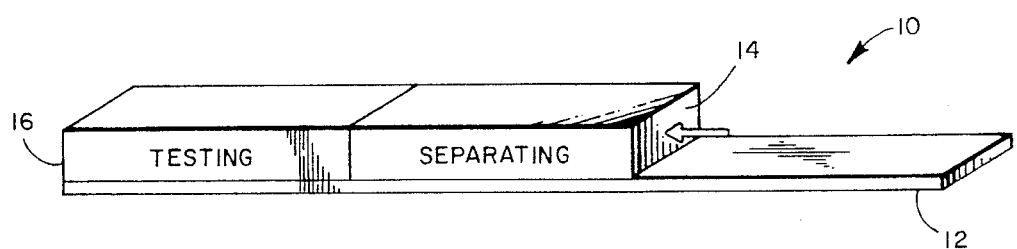
FIG. 1 is a perspective view of a test device of the present invention wherein the filter pad to separate the cellular components of a whole blood sample from the plasma or serum and the test pad to assay the plasma or serum for a predetermined soluble constituent are arranged in a longitudinally aligned configuration.

In accordance with the method of the present invention the cellular components of a whole blood sample first are separated from the plasma or serum; then, the undiluted and unaltered plasma or serum is assayed for a predetermined soluble constituent, or constituents, without any further manipulative steps. According to the method and device of the present invention, a small blood sample, usually a pin prick amount (approximately 10 microliters), is sufficient to achieve separation of the cellular components and to assay the serum or plasma, as opposed to the large milliliter size blood samples required in the centrifuge method of separation. Furthermore, the method and device of the present invention eliminate the manipulative steps, like dilution, that can cause technician error or technician contact with a potentially infectious whole blood sample.

Surprisingly and unexpectedly, the test device of the present invention essentially completely separates the highly-colored and interfering red blood cells from the plasma and serum for a predetermined soluble constituent, usually within less than a minute, without the additional time-consuming and potentially unhealthful manipulative steps of either centrifugation, decantation or plasma or serum dilution. The method of the present invention provides rapid and reliable whole blood assays on undiluted, unaltered, and noncontaminated plasma or serum samples with a simple and inexpensive test strip device. Overall, the method and device of the present invention are ideally suited for routine blood assays at home, in small laboratories and in private medical offices, wherein the number of assays usually is relatively low, but accurate results are nevertheless required in a short time period (i.e., less than one minute).

As will become apparent from the following detailed description of the invention, the method and device of the present invention are suited especially for blood assays utilizing chromogenic responses to determine the presence or concentration of the various soluble constituents of whole blood. Therefore, it is of primary importance to remove the highly-colored red blood cells from the whole blood sample in order to achieve an accurate and reliable detection and measurement of the chromogenic response. Furthermore, any method or device for separating the cellular components of whole blood from the plasma or serum should quickly and efficiently achieve cell separation; remove only the cellular components and not the soluble plasma or serum constituents; avoid contamination of the plasma or serum with interfering, soluble ions or molecules; and minimize or eliminate hemolysis, wherein the red blood cells rupture and release their highly-colored components to the plasma or serum. Due to the potentially infectious nature of the blood or other biological sample, the method and device also should minimize, or eliminate, human contact with the test sample.

In accordance with an important feature of the present invention, it has been found that the cellular components of whole blood are effectively separated from the essentially-colorless plasma or serum by allowing the whole blood sample to contact and permeate through a filter pad comprising a suitable carrier matrix including a separating reagent composition. The separating reagent composition comprises: a) a separating reagent, like an agglutinin, such as a lectin; or a coagulant, such as a thrombin or a thrombin-like compound; or a combination thereof, and b) a nonhemolytic surfactant. The separating reagent composition enhances any inherent ability possessed by the carrier matrix in removing the highly-colored cellular components from the whole blood sample to yield a straw-colored plasma or serum that is amenable to a simple and accurate determination of its soluble components.

The filter pad of the test device is in contact with a test pad of the test device. As the whole blood permeates through the filter pad, the cellular components are separated from the whole blood sample, and collected and retained in the filter pad. The unaltered serum or plasma then advances to, and saturates, a test pad that is in contact with the filter pad. The test pad comprises a suitable substrate material incorporating an indicator reagent composition that interacts with a predetermined plasma or serum constituent of interest to give a detectable or measurable response. After the test pad is saturated by the plasma or serum, the test pad is examined for a response, such as a chromogenic response, either visually or by instrument, to a predetermined plasma or serum constituent.

Generally, the filter pad of the present invention comprises a carrier matrix that has an inherent ability to filter a portion of the cellular components from a whole blood sample. The carrier matrix is normally a hydrophilic, absorbent matrix capable of separating a portion of the cellular components of whole blood from the plasma or serum, and amenable to incorporating a separating agent composition to facilitate the essentially complete separation of the cellular components from the whole blood sample. In addition to collecting and retaining the separated cellular components, the carrier matrix permits the plasma or serum to permeate through the filter pad essentially unimpeded to contact the test pad.

The carrier matrix also should permit the whole blood sample to permeate through the filter pad at a sufficient rate to allow adequate time for efficient red blood cell separation, yet rapidly enough to obtain blood assays relatively quickly. In addition, the carrier matrix should not promote hemolysis, contaminate the serum or plasma or plasma-extraction of components of the carrier matrix, remove serum or plasma constituents by chemical or physical interactions, or appreciably alter the undiluted plasma or serum in a way to make the subsequent assays inconclusive, inaccurate or doubtful.

Therefore, the filter pad of the present invention normally comprises a hydrophilic carrier matrix, possessing the above-mentioned characteristics, and a separating reagent composition. The carrier matrix allows the blood to move, in response to capillary forces, through the filter pad. The cellular components are separated from the plasma or serum by the separating reagent composition and the carrier matrix, and are retained by the filter pad. The essentially unaltered serum or plasma then continues advancing through the filter pad to contact and saturate a test pad that is in contact with the filter pad.

The carrier matrix can be any hydrophilic material that allows only the essentially cell-free and straw-colored plasma or serum to pass through the filter pad to contact the test pad for analysis of a particular soluble substituent. Suitable hydrophilic carrier matrices include bibulous and nonbibulous, fibrous and nonfibrous matrices, like hydrophilic inorganic powders, such as, silica gel, alumina, diatomaceous earth and the like; sponge materials; argillaceous substances; cloth; hydrophilic natural polymeric materials, particularly cellulosic material, like cellulosic beads, and especially fiber-containing papers such as filter paper or chromatographic paper; and synthetic or modified naturally occurring polymers, such as cellulose acetate, polyvinyl chloride, polyacrylamide, a polyacrylate, a polyurethane, crosslinked dextran, agarose and other such crosslinked and noncrosslinked water-insoluble hydrophilic polymers. Similarly, other suitable carrier matrices include fibrous and nonfibrous matrices like a glass fiber matrix; and synthetic polymers, like polypropylene, polyethylene, nylon, polyvinylidene fluoride and a polysulfone. A hard, porous plastic also is useful as the carrier matrix as long as the plastic is sufficiently porous to allow the plasma or serum to permeate through the plastic and contact the test pad.

Therefore, the carrier matrix has a pore size of between about $0.1\mu$ (micron) and about $50\mu$, and preferably between about $0.3\mu$ and about $10\mu$, to achieve efficient separation of the cellular components and to permit the serum or plasma to advance through the filter pad. To achieve the full advantage of the present invention, the carrier matrix has a pore size ranging from about $0.5\mu$ to about $8\mu$.

The filter pad of the test device can include more than one carrier matrix, and the carrier matrices can have different physical characteristics and can be different chemical compositions or a mixture of chemical compositions. The carrier matrix, or matrices, of the filter pad also can vary in regards to smoothness and roughness combined with hardness and softness. However, in every instance, the carrier matrix, or matrices, of the filter pad separates and collects the cellular components of whole blood, and allows the plasma or serum to pass through the filter pad to the test pad unaltered and essentially unimpeded. Therefore, regardless of the exact composition of the carrier matrix, or matrices, the primary considerations are incorporation of a separating reagent composition, separation of the cellular components of a test sample, collection and retention of the cellular components of whole blood and transmittal of substantially unaltered and undiluted plasma or serum.

To achieve the full advantage of the present invention, the carrier matrix comprises a cellulosic material, such as paper, and preferably filter paper; or a glass fiber matrix. Both a filter paper and a glass fiber matrix possess the properties required of a suitable carrier matrix of the present invention, plus the advantage of abundant supply, favorable economics, and a variety of suitable grades. Furthermore, filter paper and glass fiber matrices are capable of suspending and positioning a separating reagent composition in the filter pad, and of separating the cellular components from whole blood.

As known to those skilled in the art, filter paper and glass fiber matrices are available in a variety of thicknesses and porosities. Since the use of the device requires the filter pad to contact the whole blood sample, and that a substantially colorless fluid must be allowed to emerge therefrom, the thickness and porosity of the carrier matrix influence the efficiency of the test device and influence the effectiveness of the separation process. The thickness and porosity of the filter pad are directly related to the inherent ability of the carrier matrix to separate the cellular components from plasma or serum and to the time required for the whole blood sample to permeate through the filter pad to separate the cellular components from the whole blood sample. Therefore, if a carrier matrix of high porosity is used, the thickness of the carrier matrix should be sufficient to allow a minimum effective contact time between the whole blood and the filter pad in order to achieve an effective separation of the cellular components of the whole blood. Conversely, if a carrier matrix of low porosity is utilized, a relatively thin layer of carrier matrix can be employed. The proper balance between carrier matrix porosity and thickness, and a judicious selection of the type and concentration of separating reagent composition incorporated into the carrier matrix, is well within the experimental techniques used by those skilled in the art of preparing a test device described in the present specification.

It has been shown that an untreated carrier matrix usually cannot separate the cellular components from whole blood effectively. If a sample of whole blood is applied to an untreated filter paper matrix, the amount of separated cellular components observed as the whole blood sample permeates through the filter paper varies with the thickness and porosity of the filter pad. For other carrier matrices, the partial separation of the cellular components from a whole blood sample also has been observed as the blood permeates through a carrier matrix having sufficient thickness and sufficiently low porosity. However, the separation of the cellular components of whole blood from plasma or serum is not observed if the carrier matrix incorporates, or otherwise is treated, with a suitable separating reagent composition, the cellular components are effectively separated and fixed in the carrier matrix as the blood sample permeates through the filter pad, and the plasma or serum advances through the filter pad to contact the test pad of the test device.

It has been found that an untreated carrier matrix having a thickness of at least about 1 mm (millimeter), and usually of at least about 1.5 mm, is necessary to effectively separate the cellular components from a whole blood sample. Such a large thickness generally is unsuitable for a filter pad in a dry phase test strip. However, if a separating reagent composition is incorporated into the carrier matrix to remove the cellular components from the serum or plasma, the thickness of the carrier matrix can be reduced to as low as about 0.2 mm, and preferably as low as about 0.3 mm. Therefore, to achieve the full advantage of the present invention, the filter pad comprises a carrier matrix in the form of a pad, having dimensions of, for example, about 0.25 cm. (centimeter) to about 1 cm by about 0.5 cm to about 2 cm and a thickness of about 0.2 mm to about 0.8 mm. The carrier matrix then has incorporated therein a separating reagent composition comprising: a) a separating reagent, like an agglutinin, such as a lectin; a coagulant, such as a thrombin or a thrombin-like compound; or a combination thereof, and b) a nonhemolytic surfactant. A filter pad of such dimensions has sufficient length, width and thickness for effective separation of cellular components within a sufficiently short time after the blood contacts one end, or the top, of the filter pad.

If a test device of the present invention has a filter pad of the above-defined dimensions, a pin-prick amount of blood, such as about 0.01 ml (milliliter), usually is a sufficient amount of sample to provide a fast and accurate assay for a predetermined soluble constituent. The blood sample can be applied to the test device dropwise or with a pipette, or preferably, the test device can contact a finger puncture and the blood sample is drawn into the test device by capillary action. Appreciably increasing the size of the filter pad substantially increases the time of separation, and also requires a larger blood sample. Furthermore, a relatively large sample of blood can be used to increase the speed of serum transfer to saturate the test pad. In accordance with another feature of the present invention, the amount of whole blood sample contacting the test device need not be precisely measured. However, care should be exercised to avoid overloading the filter pad with an excessively large blood sample such that a portion of whole blood contacts the test pad of the test device.

As will be discussed more fully hereinafter, the filter pad comprises a carrier matrix incorporating a separating reagent composition to achieve essentially complete separation of the cellular components of whole blood from the plasma or serum. However, the prior art separating reagents, such as the inorganic salts and amino acids disclosed by Fetter in U.S. Pat. Nos. 3,552,925 and 3,552,928, can introduce contaminating ions or molecules into the serum or plasma, and assayable plasma or serum constituents also are separated from the plasma or serum.

Therefore, in accordance with an important feature of the present invention, a separating reagent composition, comprising: a) a separating reagent selected from the group consisting of an agglutinizing agent, a coagulating agent and combinations thereof and b) a nonhemolytic surfactant, is incorporated into the carrier matrix such that the cellular components of the whole blood agglutinate or are trapped as the blood sample chromatographs through the filter pad. The agglutinated or trapped cells become fixed, and are collected within the filter pad, as the plasma or serum continues advancing through the filter pad to eventually contact and saturate the test pad of the test device.

As will become apparent from the following detailed description of the invention, various lectins, thrombins or thrombin-like compounds, used individually or in combination, agglutinate or coagulate the cellular components of whole blood to fix the cellular components within the filter pad, and allow the undiluted serum or plasma to advance, unaltered and essentially unimpeded, to the test pad of the test device. In addition, the lectins, thrombins or thrombin-like compounds present in the separating reagent composition do not promote excessive hemolysis. Therefore, the red blood cells do not rupture and their highly-colored components do not interfere with and mask the chromogenic assays. Furthermore, it will become apparent that including a nonhemolytic surfactant in the separating reagent composition allows the amount of agglutinin or coagulant incorporated into the carrier matrix to be reduced substantially, thereby providing a more economical test device that yields more reproducible assays results.

The preferred agglutinin present in the separating reagent composition is a lectin. The lectins are proteins or glycoproteins that are known to agglutinate, or clump, cells and precipitate complex carbohydrates. Lectins are isolated from a wide variety of natural sources, including seeds, plant roots, bark, fungi, bacteria, seaweed, sponges, fish eggs, invertebrate and lower vertebrate body fluids, and mammalian cell membranes. The lectins are often blood group specific, and have been used in blood grouping, polyagglutination studies, and various histochemical studies of normal and pathological conditions. The lectins used in the present invention present invention preferably are not specific to a particular blood group or type, or the general utility of the method and device of the present invention could be limited. Therefore, lectins showing no specificity of blood grouping and that are suitable for use in the present invention include, but are not limited to, *Abrus precatorius* (abrin, Jequirty bean), *Agaricus bisporus* (mushroom), *Bauhinia purpurea* (camels foot tree), *Caragana arborescens* (Siberian pea tree), *Cicer arietinum* (chick pea), *Codium fragile* (Green marine algae), *Canavalia ensiformis* (Con A, Concanavalin A, Jack bean), *Datura stramonium* (jimson weed), *Glycine max* (Soybean), *Lathyrus odoratus* (Sweet Pea), *Lens culinaris* (Lentil), *Limulus polyphemus* (Horseshoe crab, Limulin), *Lycopersicon esculentum* (Tomato), *Maclura pomifera* (Osage orange), *Mycoplasma gallisepticum, Naja mocambique mocambique* (cobra venom), *Naja naja kaouthia* (cobra venom), *Perseau americana* (Avocado), *Phaseolus coccineus* (Scarlet runner bean), *Phaseolus vulgaris* (Red Kidney bean), *Phytolacca americana* (Pokeweed), *Pisum sativum* (garden pea), *Pseudomonas aeruginosa, Psophocarpus tetragonolobus* (winged bean), *Ricinus communis* (Castor bean), *Robinia pseudoacacia* (black locust, false acacia), *Sambucus nigra* (elder), *Solanum tuberosum* (Potato), *Triticum vulgaris* (Wheat germ), *Vicia faba* (fava bean, broad bean), *Vicia sativa, Vigna radiata* (Mung bean), *Viscum album* (European mistletoe), *Wisteria floribunda* (Japanese wisteria), and other like blood type nonspecific lectins.

The preferred lectins incorporated into the carrier matrix of the filter pad are the lectin from Concanavalin A (jack bean), the lectin from *Solanum tuberosum* (potato), the lectin from *Triticum vulgaris* (wheat germ), the lectin from *Bauhinia purpurea* (camels foot tree) and the lectin from *Phytolacca americana* (pokeweed). To achieve the full advantage of the present invention, the filter pad had incorporated therein the lectin from potato (*Phytolacca americana*).

In addition to, or in place of, the abovedescribed lectins, a coagulating agent also can be used to separate the cellular components of whole blood from the serum or plasma. Specifically, the enzyme thrombin, from bovine plasma, has been incorporated into a carrier matrix to provide a filter pad of the present invention that successfully separates serum or plasma from whole blood samples. The bovine thrombin effectively promotes blood clotting such that the red blood cells are removed from the whole blood as the blood permeates through the filter pad. Other thrombins useful according to the method of the present invention include, but are not limited to, human thrombin, horse thrombin, goat thrombin, mouse thrombin, rat thrombin, pig thrombin, sheep thrombin, and combinations thereof.

Furthermore, in addition to, or in place of, the abovedescribed lectins and thrombins, a coagulating agent that behaves similar to a thrombin can be used to effect separation of the serum or plasma from the cellular components of whole blood. Such thrombin-like compounds include, but are not limited to, the enzymes acutase, agkistrodon contortrix, ancrod, atroxin, crotalase and combinations thereof. Such compounds are thrombin-like in behavior and effectively promote blood clotting. It also has been found unnecessary to immobilize the thrombin, the lectin or the thrombin-like compound onto the carrier matrix, and that an effective separation of the cellular components from a whole blood sample can be achieved by using a lectin, a thrombin, a thrombin-like compound or a combination thereof.

As previously described, the device of the present invention includes a filter pad, comprising a carrier matrix incorporating a separating agent composition, to separate the cellular components from the serum or plasma of an undiluted whole blood sample. To achieve the full advantage of the present invention, the filter pad comprises a carrier matrix incorporating a blood separating reagent composition including a) a thrombin, a thrombin-like compound or a blood group non-specific lectin and b) a nonhemolytic surfactant. A suitable nonhemolytic surfactant substantially increases the efficienly of the lectin, thrombin or thrombin-like compound in separating the cellular components from a whole blood sample; does not interact with or retain the soluble constituents of the serum or plasma to alter the concentration of a soluble plasma constituent; does not hemolyze the red blood cells of the test sample; is not appreciably extracted by the plasma or serum from the filter pad and thereby transferred to the test pad; promotes a uniform wetting of the filter pad by the test sample, thereby promoting a more uniform response in the test pad; and does not otherwise interfere in the assay for a predetermined soluble plasma or serum constituent.

A preferred nonhemolytic surfactant is a nonionic nonhemolytic surfactant. A nonionic nonhemolytic surfactant is electrically neutral, thereby precluding anionic and cationic interactions between the nonhemolytic surfactant and various soluble test sample constituents or reagents in the test pad. For example, the cation of an anionic surfactant may alter the concentration of a particular cationic analyte, like potassium ion, by ion exchange to provide an erroneous assay; and a cationic surfactant, like some quaternary ammonium salts, can denature an enzyme like lactose dehydrogenase, or precipitate a protein, to provide an erroneous assay. Such anion and cation interactions are prevented by including a nonionic nonhemolytic surfactant in the separating reagent composition. However, it should be understood, and will be demonstrated, that an anionic surfactant or an cationic surfactant can be included in the separating reagent composition as long as the surfactant does not promote hemolysis, effectively separates the cellular components from whole blood and does not interfere with the assay to provide an erroneous result.

It further has been found that nonionic nonhemolytic surfactants including ethoxy or propoxy moieties are especially useful in the method of the present invention. Nonionic nonhemolytic surfactants, wherein the hydrophilic portion of the surfactant includes from two to about 100 moles, and preferably from about 5 to about 50 moles, of ethylene oxide, propylene oxide or a combination thereof, and having an HLB value (hydrophilic-lipophilic balance value) in the range of from about 5 to about 25, are especially preferred. To achieve the full advantage of the present invention, the nonhemolytic surfactant, either nonionic, anionic or cationic, has an HLB value in the range of from about 10 to about 20. The hydrophobic portion of the surfactant can be, for example, an alkyl phenol wherein the alkyl group included from about four to about twenty carbon atoms, like isooctyl phenol or nonyl phenol; a fatty alcohol including from about 8 to about 22 carbon atoms, like lauryl alcohol, cetyl alcohol or stearyl alcohol; a fatty acid, a fatty amide or a fatty amine including from about 8 to about 22 carbon atoms; a natural oil, either animal or vegetable, like castor oil; a silicone, like a polydimethylsiloxane; a fatty ester of a polyol, like the $C_8$ to $C_{22}$ esters of glycerol or sorbitol; and similar hydrophobes known to persons skilled in the art of surfactants.

Specific examples of nonionic nonhemolytic surfactants include, but are not limited to, CREMOPHOR® EL (PEG-36 castor oil), an ethoxylated castor oil available from BASF Corp., Wyandotte, Mich.; TRITON X-405 (octoxynol 40) and TRITON X-45, (octoxynol 5), octylphenol ethoxylated with about 40 moles and 5 moles of ethylene oxide, respectively, available from Rohm and Haas Co., Philadelphia, Pa.; PLURONIC L-64 (poloxamer 184), a propylene oxide/ethylene oxide copolymer available from BASF Corp., Wyandotte, Mich.; TWEEN 20 (polysorbate 20), a sorbitan monolaurate including about twenty moles of ethylene oxide; and the SILWET® surfactants (dimethicone copolyols), the ethylene oxide or propylene oxide modified polymethylsiloxanes available from Union Carbide Corp., Danbury, Conn. Other suitable nonionic nonhemolytic surfactants include, but are not limited to, $C_{11-15}$ pareth-12, $C_{12-15}$ pareth-9, ceteareth-27, ceteth-30, laureth-23, oleth-15, nonoxynol-6, nonyl nonoxynol-10, PEG-20 laurate, PEG-36 oleate, PEG-44 sorbitan laurate, PEG-30 stearate, steareth-27, octoxynol-10, PEG-11 cocamide, PEG-15 cocamine, PEG-15 tallow amine, PEG-20 hydrogenated castor oil, PPG-5-ceteth 20, PPG-myreth-11, steareth-10, trideceth-15, and polysorbate 80. Numerous other nonionic nonhemolytic surfactants are known to those skilled in the art of designing diagnostic test devices; and numerous nonionic nonhemolytic surfactants incorporating ethylene oxide or propylene oxide moieties, or a combination thereof, are listed in *McCutcheon's Emulsifiers and Detergents*, 1989 Annual Edition, McCutcheon Division, MC Publishing Co., Glen Rock, N.J., and in *CTFA Cosmetic Ingredient Handbook*, 1st Edition, The Cosmetic, Toiletry and Fragrance Association (1988), pages 87 through 94, hereby incorporated by reference.

In addition to nonionic nonhemolytic surfactants, an anionic nonhemolytic surfactant also can be used in the method and device of the present invention. The preferred anionic nonhemolytic surfactants include from two to about 100 moles, and most advantageously from about 5 to about 50 moles, of ethylene oxide, propylene oxide or a combination thereof, and an HLB value in the range of from about 5 to about 25, and most advantageously from about 10 to about 20. Especially useful anionic nonhemolytic surfactants are the ethoxylated or propoxylated phosphate surfactants and the ethoxylated or propoxylated carboxylate surfactants. Such anionic surfactants can be included in the separating reagent composition in the acid form, and thereby do not include a cation that alters the concentration of a particular cationic analyte, like potassium ion. These anionic nonhemolytic surfactants also can be included in the separating reagent composition in the anionic form, as long as the cation of the anionic nonhemolytic surfactant does not interfere in the assay for a particular analyte. As will be demonstrated more fully hereinafter, anionic surfactants that do not include ethoxy and/or propoxy moieties do not appreciably improve the ability of a carrier matrix to separate the cellular components from a whole blood sample.

Therefore, examples of suitable anionic nonhemolytic surfactants that can be utilized in the method and device of the present invention include, but are not limited to, the acidic and the anionic forms of $C_{11-17}$ pareth-7 carboxylic acid, $C_{12-13}$ pareth-5 carboxylic acid, $C_{12-15}$ pareth-7 carboxylic acid, ceteareth-25 carboxylic acid, deceth-7 carboxylic acid, isosteareth-6 carboxylic acid, isosteareth-11 carboxylic acid, coceth-7 carboxylic acid, laureth-5 carboxylic acid, laureth-10 carboxylic acid, trideceth-4 carboxylic acid, trideceth-7 carboxylic acid, trideceth-15 carboxylic acid, trideceth-19 carboxylic acid, $C_{12-15}$ pareth-2 phosphate, ceteareth-4 phosphate, deceth-4 phosphate, dilaureth-10 phosphate, dioleth-8 phosphate, laneth-4 phosphate, laureth-3 phosphate, laureth-8 phosphate, nonoxynol-6 phosphate, nonoxynol-9 phosphate, nonoxynol-10 phosphate, nonyl nonoxynol-7 phosphate, nonyl nonoxynol-9 phosphate, nonyl nonoxynol-10 phosphate, nonyl nonoxynol-15 phosphate, nonyl nonoxynol-24 phosphate, oleth-3 phosphate, oleth-4 phosphate, oleth-10 phosphate, oleth-20 phosphate, potassium octoxynol-12 phosphate, PPG-5-ceteth-10 phosphate, PPG-10 cetyl ether phosphate, triceteareth-4 phosphate, triceteth-5 phosphate, trideceth-6 phosphate, trilaneth-4 phosphate, trilaureth-4 phosphate, trioleth-8 phosphate, and combinations thereof. It should be understood that the phosphate surfactants are complex mixtures of mono-, di- and tri-esters of phosphoric acid, and therefore include both a major amount of the anionic mono- and di-ester forms and a minor amount of the nonionic tri-ester form. Furthermore, the nonionic and anionic nonhemolytic surfactants can be included in the separating reagent composition either alone or in combination. A particularly useful anionic nonhemolytic surfactant is CRODAFOS SG (PPG-5-ceteth-10 phosphate), a complex mixture of esters of phosphoric acid and polyethoxylated and polypropoxylated cetyl alcohol, available from Croda, Inc., New York, N.Y.

It has been found that incorporating an aqueous separating reagent composition, including from about 0.05% to about 3%, and preferably from about 0.3% to about 1.5%, by weight of a nonhemolytic surfactant and from about 4 units to about 4,000 units of a lectin or from about 90 NIH units to about 900 NIH units of a thrombin or a thrombin-like compound, or a combination thereof, into a suitable carrier mixture provides a filter pad of the present invention. Surprisingly, by incorporating both a nonhemolytic surfactant and an agglutinin or a coagulant into a carrier matrix, the amount of agglutinin or coagulant needed to effect an essentially complete separation of the cellular components from the plasma or serum is reduced significantly. It has been found that a carrier matrix including only an agglutinin or a coagulant requires from about 55 units to about 40,000 units of agglutinin, or from about 90 NIH units to about 900 NIH units of coagulant, per $cm^3$ of carrier matrix to essentially completely separate the cellular components from a whole blood sample. However, if a nonhemolytic surfactant is included in the separating reagent composition, then the amount of agglutinin, or the amount of coagulant, present in the carrier matrix can be reduced by an amount of 80%, without adversely affecting the ability of the agglutinin or the coagulant to separate the cellular components from the whole blood sample.

Therefore, a more economical test device is provided because less of the expensive agglutinin or coagulant is incorporated into the filter pad; more reproducible assay results are achieved because less of the hard to reproduce coagulant or agglutinin is present in the filter pad; and blood samples including more than 50% at hematocrit, i.e., cellular components, are separated essentially completely into a cellular component and serum or plasma, thereby providing more sensitive and accurate assays because the interfering effects of the cellular components are effectively eliminated. In accordance with another important feature of the present invention, it will be demonstrated that in contrast to prior art assays of whole blood, the present invention essentially eliminates the amount of cellular components in the whole blood sample as a parameter in the assay for a predetermined soluble constituent of the plasma or serum. Therefore, by including from about 0.05% to about 3% by weight of a nonhemolytic surfactant in a separating reagent composition used to treat the carrier matrix, the amount of coagulant necessary to effect an essentially complete separation of the cellular components from the whole blood is in the range of from about 20 NIH units to about 200 NIH units, or in the amount of agglutinin is in the range of from about 5 units to about 100 units, per $cm^3$ of matrix.

In accordance with the method of the present invention, a whole blood sample contacts the filter pad of the test device, whereby the cellular components of the whole blood are separated from the serum or plasma as the blood sample advances through the filter pad. The undiluted and unaltered serum or plasma then advances through the filter pad to contact and saturate a test pad that is in contact with the filter pad. The test pad of the test device comprises a suitable substrate material including an indicator reagent composition suitable for a particular assay of interest. After the test pad is saturated with the plasma or serum, the test pad then is examined, either visually or instrumentally, for a response to the particular analyte of interest.

Specifically, the positioning of the filter pad and the test pad is better understood by reference to FIGS. 1 through 4. FIG. 1 is a perspective view of a test device 10 including a filter pad 14 and a test pad 16 securely adhered to a support strip or handle 12. The filter pad 14 and the test pad 16 are aligned longitudinally and are in contact. The filter pad 14 has incorporated therein a separating reagent composition including an agglutinin or a coagulant and a nonhemolytic surfactant, and the test pad 16 has incorporated therein a suitable testing reagent. As will become more apparent hereinafter, in order to facilitate the quantitative determination of a predetermined plasma or serum constituent, it is preferred that the support strip or handle 12 be manufactured from a hydrophobic material, either opaque or transparent.

A test sample is introduced to the test device 10 in the direction of the arrow at one end of the filter pad 14 and a portion of the test sample passes through the filter pad 14 to contact a test pad 16. After the essentially cell-free plasma or serum contacts the test pad 16, an interaction between the testing reagent and the predetermined soluble constituent of interest produces a detectable change, like a chromogenic change, in the test pad 16. The test pad 16 then is examined for the response, either visually or by instrument, and the intensity and degree of the response are correlated to the amount of predetermined soluble constituent in the test sample. The cellular components of the test sample are fixed in the filter pad 14, and do not interfere with the detectable change in the test pad 16. It also is envisioned that the longitudinal alignment of the filter pad 14 and the test pad 16 on the support strip 12 can be transposed. In this transposed configuration, the test device 10 can be dipped into a whole blood sample or can contact a finger puncture to introduce the test sample to the test device 10.

Figure 2:
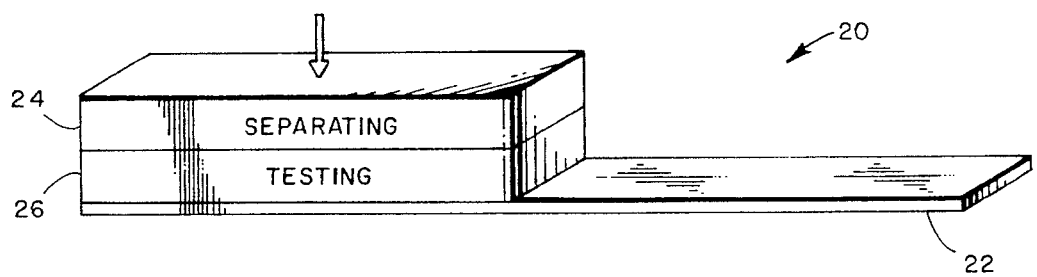
FIG. 2 is a perspective view of another embodiment of a test device of the present invention wherein the filter pad and the test pad are arranged in a laminar configuration.

Another, and preferred, configuration of the test sample is illustrated in FIG. 2, showing a test device 20 wherein a filter pad 24, incorporating a separating reagent composition comprising an agglutinin or a coagulant and a nonhemolytic surfactant into a carrier matrix, and a test pad 26 are in a laminar configuration. The bottom surface of the test pad 26 is securely adhered to a transparent handle 22 and the top surface of the test pad 26 is secured to the bottom surface of the filter pad 24. A blood sample is introduced on the top surface of the filter pad 24 in the direction of the arrow. After separation of the cellular components from the blood sample by the filter pad 24, the serum or plasma migrates to the test pad 26. The plasma or serum contacts the indicator reagent composition incorporated into the test pad 26, and the presence or concentration of a predetermined soluble constituent in the plasma or serum is determined by examining the test pad 26 for a detectable response through the transparent handle 22.

Figure 3:
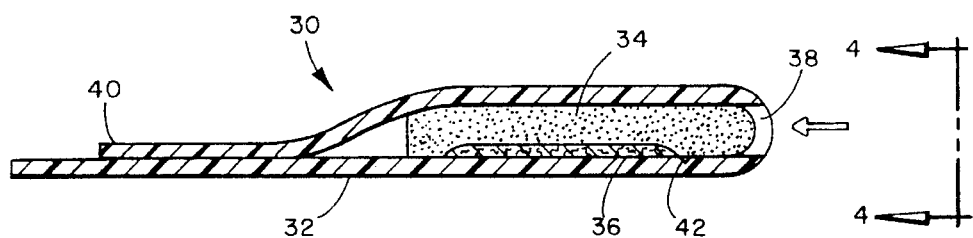
FIG. 3 is a partial side view of yet another embodiment of a test device of the present invention wherein the filter pad and the test pad are arranged in a laminar configuration and the filter pad is detachable from the test device.
Figure 4:
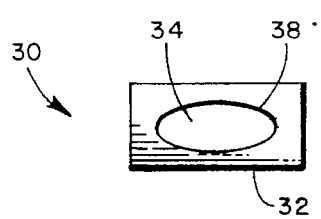
FIG. 4 is an end view of the test device of FIG. 3 taken in the direction of arrows 4—4 of FIG. 3 showing the sample port for introducing the whole blood or other sample to the test device.

Another embodiment of the present invention is illustrated in FIGS. 3 and 4. FIG. 3 shows a test device 30 including a filter pad in releasable contact with a test pad 36. Both the filter pad 34 and the test pad 36 are securely adhered to a support strip or handle 32. The test sample is introduced to the test device 30 in the direction of the arrow at the curved end of the test device 30 through a sample port 38 to first contact and permeate through the filter pad 34. The filter pad 34 separates the cellular components from the whole blood sample, and the plasma or serum advances through the filter pad 34 to contact the test pad 36. After the plasma or serum saturates the test pad 36, and upper free edge 40 of the support strip handle 32 is pulled to separate the filter pad 34 from the test pad 36. By further pulling the upper free edge 40, the support strip of handle 32 is disjoined at a notch 42 to detach the filter pad 34 and the upper free edge 40 from the test device 30 and to expose the test pad 36 for visual or instrumental examination of a response to a predetermined soluble constituent of interest. FIG. 4 is an end view of the test device 30 taken in the direction of arrows 4—4 of FIG. 3, and more clearly shows the sample port 38 for introducing the test sample to the test device 30.

To achieve the full advantage of the present invention, for the embodiments illustrated in FIGS. 1 through 3, the filter pad 14 (24, 34) and the test pad 16 (26, 36) preferentially incorporate the separating reagent composition and indicator reagent composition, respectively, before the filter pad 14 (24, 34) and the test pad 16 (26, 36) are adhesively secured to the support strip or handle 12 (22, 32). Alternatively, the separating reagent composition or the indicator reagent composition can be incorporated into the filter pad 14 (24, 34) and the test pad 16 (26, 36) after the filter pad 14 (24, 34) and the test pad 16 (26, 36) are adhesively secured to the support handle 12 (22, 32), but before the filter pad 14 (24, 34) and the test pad 16 (26, 36) are positioned in contact.

Several other alternate embodiments of test devices similar to the test devices illustrated in FIGS. 1–3 also are envisioned. For example, the filter pad and test pad can vary relatively in size to account for a larger or a smaller blood sample, with the relative sizes of the two pads depending upon the predetermined soluble constituent of interest and the blood sample size needed to assay for that constituent. In another embodiment, the test pad and filter pad are a single pad, wherein one area of the pad incorporates the separating reagent composition and a second area of the pad incorporates the indicator reagent composition. Another embodiment envisions a multideterminant test strip wherein a single filter pad is positioned over a plurality of test pads such that the plasma or serum of a single small blood sample can be assayed for more than one soluble constituent.

EXAMPLE 1

INCORPORATING THE SEPARATING REAGENT COMPOSITION INTO THE CARRIER MATRIX OF THE FILTER PAD

The agglutinin, coagulant or combination thereof, such as bovine thrombin, the lectin from Solanum tuberosum, the lectin from concanavalin A, the lectin from Phytolacca americana, or the thrombin-like enzyme acutase is solubilized in normal, or isotonic, saline solution. Then from about 0.05% to about 3%, and preferably from about 0.5% to about 1.5%, by weight of a nonhemolytic surfactant, such as CREMOPHOR® EL, is added to the saline solution including the agglutinin or coagulant to form a separating reagent composition. The separating reagent composition then is incorporated into a carrier matrix, such as filter paper, like WHATMAN CCP500 filter paper, or a glass fiber matrix, like WHATMAN PD107, available from Whatman Ltd., Maidenshead, Kent, U.K., either by immersing the carrier matrix into the separating reagent composition or by spraying the separating reagent composition onto sheets or precut strips of the carrier matrix. The carrier matrix incorporating the separating reagent composition then is dried at about 50° C. in an oven for about 20 minutes to about 40 minutes to provide a filter pad of the present invention.

It is not necessary to immobilize the thrombin, thrombin-like compound or lectin onto the carrier matrix when incorporating the separating reagent composition into the carrier matrix as in Example 1. The simple drying technique is sufficient to maintain the lectin, thrombin or thrombin-like compound, and the nonhemolytic surfactant, in place within the carrier matrix for separation of the cellular components from a whole blood sample. The filter pad, after appropriate sizing, e.g., 0.5 cm×1.0 cm, then can be secured to either a transparent or an opaque, hydrophobic plastic handle, such as the support strip or handle 12 in FIG. 1, or to the test pad, such as to the test pad 26 in FIG. 2.

In the examples discussed below, the filter pad incorporating the nonhemolytic surfactant and the agglutinin or the coagulant is an element of a multilayered test device as illustrated in FIG. 2. A whole blood sample contacts the top surface of the filter pad 24 of test device 20 in FIG. 2, i.e., in the direction of the arrow, and the filter pad 24 filters and agglutinates or coagulates the cellular components of the whole blood sample, thereby allowing the essentially unaltered serum or plasma to contact the test pad 26 and interact with the indicator reagent composition incorporated therein. A response, such as a chromogenic response, is detected by examining, either visually or by instrument, the bottom surface of test pad 26 in contact with the transparent support 22.

As previously stated, in prior methods of separating of plasma or serum from whole blood that utilized an agglutinin or a coagulant, a relatively large amount of agglutinin or coagulant was required. Furthermore, an especially large amount of agglutinin or coagulant was required when the blood sample is greater than about 50% hematocrit. Therefore, because the normal hematocrit value for males is from about 40% to about 54%, and for females is from about 37% to about 47%, a large amount of agglutinin or coagulant usually is needed to effectively separate the cellular components from whole blood.

Commercially-available agglutinins and coagulants also are expensive because purification procedures require a large quantity of starting material and produce a small yield of agglutinin or coagulant. In addition, it is difficult to reproduce the purity of an agglutinin or coagulant from purification batch to purification batch, and therefore the activity of the agglutinin or coagulant can vary. This variation in purity, and therefore activity, can cause irreproducible assay results if large amounts of an agglutinin or a coagulant are incorporated into the filter pad.

Accordingly, if the amount of agglutinin or coagulant incorporated into the filter pad can be reduced, without adversely affecting the ability of the filter pad to separate the cellular components of a whole blood sample from the plasma or serum, the resulting test device would be more economical and would provide more reproducible assay results. Surprisingly and unexpectedly, the present invention, wherein a nonhemolytic surfactant is incorporated into the carrier matrix of the filter pad in conjunction with an agglutinin or coagulant, allows the amount of agglutinin or coagulant incorporated into the test pad to be reduced substantially, without adversely affecting the separation of cellular components from the whole blood sample.

To demonstrate the new and unexpected results achieved by incorporating a separating reagent composition comprising a nonhemolytic surfactant and an agglutinin or a coagulant, into a suitable carrier matrix to provide a filter pad of the present invention, the following multilayered test strips, including a transparent plastic handle, were prepared. The test strips comprised a test pad including a filter paper substrate incorporating the test reagents necessary to assay for glucose, and a filter pad comprising two layers of a glass fiber matrix having incorporated therein the lectin from Solanum tuberosum and varying concentration of the nonhemolytic surfactant CREMOPHOR EL®, an ethoxylated castor oil. The top glass fiber matrix layer comprised WHATMAN PD008 glass fiber and the second glass fiber matrix comprised WHATMAN PD107 glass fiber. The lectin and CREMOPHOR EL® were incorporated into the glass fiber matrix layers from an aqueous separating reagent composition including 0.2 mg/mL (milligram per milliliter) of the lectin Solanum tuberosum and either 0%, 0.1%, 0.3% or 0.6% by weight of CREMOPHOR EL®. The test strips were used to assay standardized blood samples including either 20% or 60% hematocrit for the soluble constituent glucose.

Figure 5:
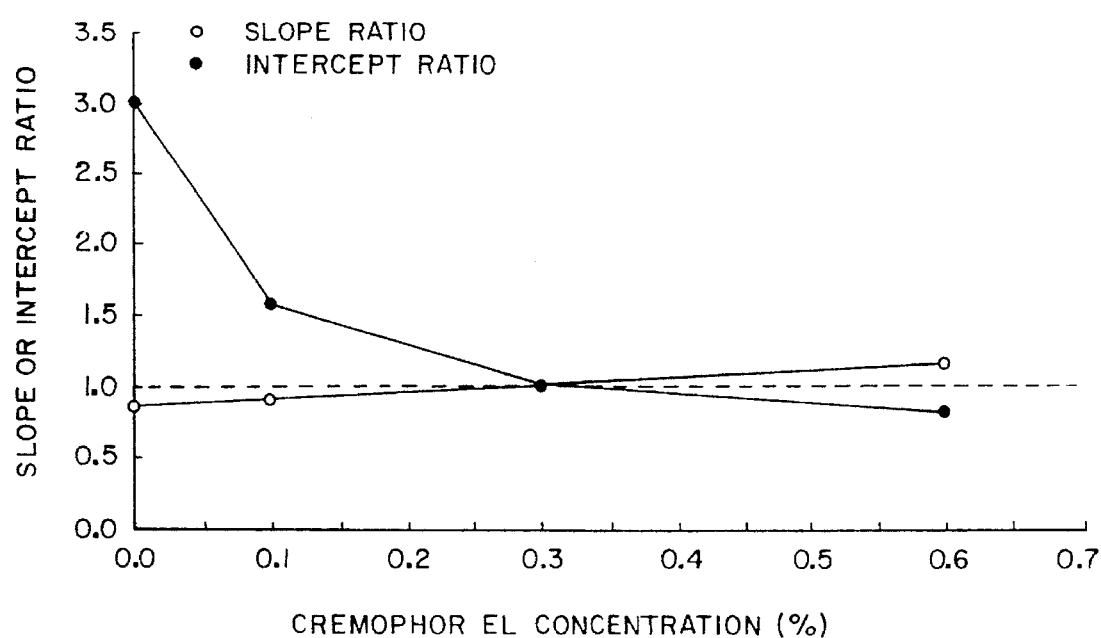
FIG. 5 is a graph including plots of concentration of nonhemolytic surfactant vs. slope ratio, and of concentration of nonhemolytic surfactant vs. intercept ratio of dose response plots for assays performed on whole blood including 60% hematocrit and whole blood including 20% hematocrit.

FIG. 5 illustrates the results of the assays, and shows that the efficiency of the agglutinin is increased by increasing the amount of nonhemolytic surfactant in the filter pad. Specifically, FIG. 5 includes a graph of the ratio of the intercept of dose response plots versus concentration of nonhemolytic surfactant, and includes a graph of the ratio of the slope of dose response plots versus concentration of nonhemolytic surfactant, for assays of whole blood samples including different amounts of hematocrit. The slope and intercept ratios of the dose response plots between assays on samples including 20% hematocrit and samples including 60% hematocrit is an indication of the effect of hematocrit on the assay. If the assay is independent of the hematocrit value, the slope and intercept ratios between the assay of 20% hematocrit sample and of 60% hematocrit sample approximates one, i.e., the dose response plots for the assays of 20% and 60% hematocrit samples essentially overlap.

For example, in a test strip including no nonhemolytic surfactant, the intercept ratio of a dose response plot for assays on blood samples including 60% hematocrit to dose response plot for assays on blood samples including 20% hematocrit is about 3 and the slope ratio is 0.9. This relatively high ratio of intercepts indicates that the assay is affected by the amount of hematocrit in the whole blood sample. Therefore, to effectively eliminate this adverse affect, the prior art teaches that the amount of agglutinin or lectin present in the filter pad should be increased. However, the present invention shows that the amount of agglutinin or lectin can be held at a low constant level (i.e., 0.2 mg/mL), and hematocrit dependence is essentially eliminated from the assay, by also including a nonhemolytic surfactant in the filter pad.

FIG. 5 illustrates that as the amount of nonhemolytic surfactant in the filter pad is increased, the ratio of intercepts and the ratio of the slopes for the dose response plots of whole blood samples including either 60% or 20% hematocrit is essentially one. FIG. 5 shows that when the amount of nonhemolytic surfactant is about 0.3% by weight of the separating reagent composition, the difference between the slope and intercept ratios between samples including 20% hematocrit and 60% hematocrit are essentially one, thereby showing that the nonhemolytic surfactant improves the efficiency of the lectin. Accordingly, the amount of hematocrit present in the test sample is essentially eliminated as an assay variable by including a nonhemolytic surfactant in the filter pad with the agglutinin or the coagulant. Surprisingly, this hematocrit dependence is eliminated by including an unexpectedly low amount of agglutinin or coagulant in the filter pad. In addition, the ratio of the slopes between dose response plots of assays performed on 60% and 20% hematocrit whole blood samples remains at about one, showing that the nonhemolytic surfactant does not adversely affect the slope of the dose response plot.

Therefore, by incorporating a nonhemolytic surfactant in the filter pad, less agglutinin or coagulant can be included in the filter pad to achieve an effective agglutination or coagulation of the cellular component in test samples having a high hematocrit value. Furthermore, assay results are more accurate because the slopes and intercepts for dose response plots of assays on test samples including a high hematocrit value or a low hematocrit value are essentially identical. Therefore, whole blood assays for a predetermined soluble constituent are more reliable because the assay results are independent of the hematocrit value of the whole blood sample.

Figure 6:
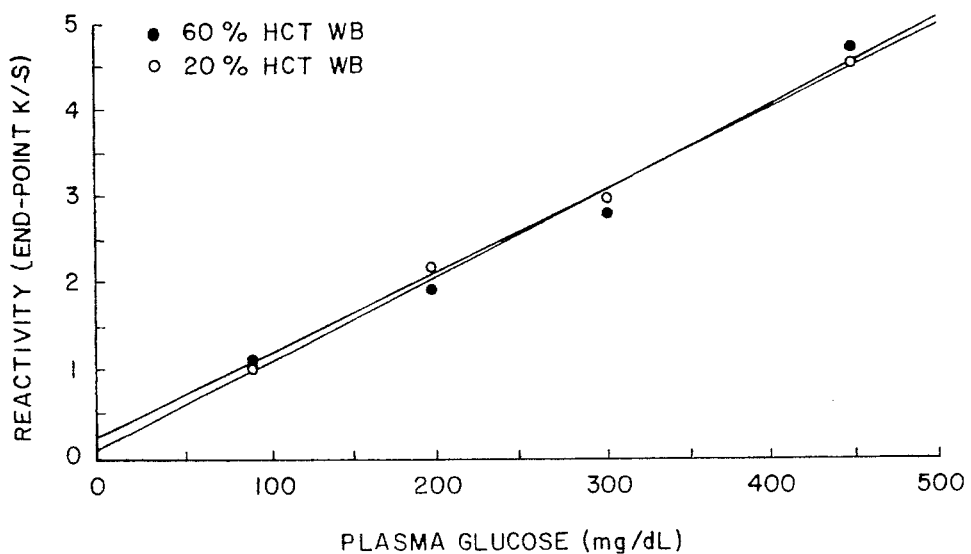
FIGS. 6 through 9 are graphs including plots of the Kubelka-Munk function (K/S) vs. the glucose concentration of standardized whole blood test samples including either 20%, 40% or 60% hematocrit (HCT) with test devices of the present invention containing various types of nonhemolytic surfactants in the filtration layer.
Figure 7:
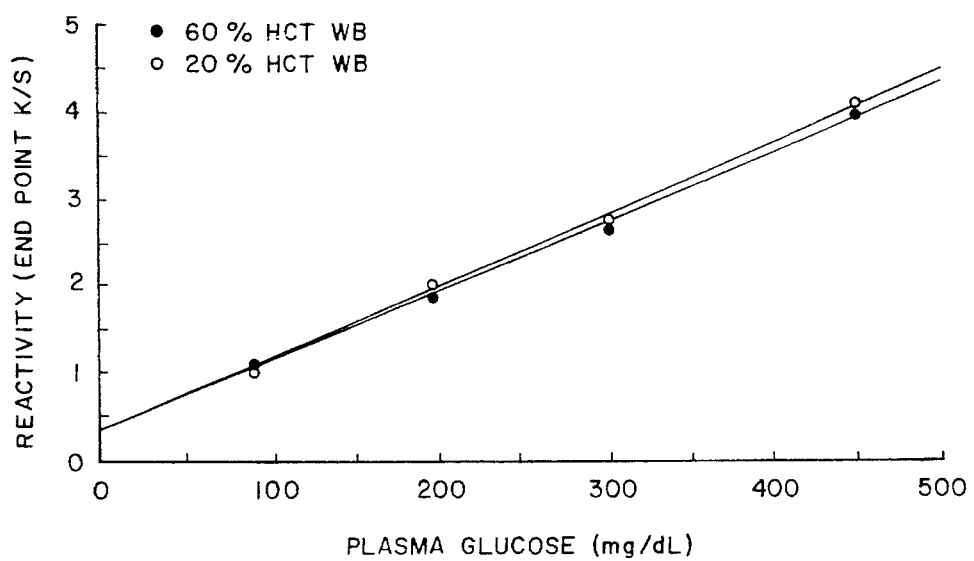

FIGS. 6 and 7 show that as the amount of nonhemolytic surfactant present in the filter pad increases, the amount of agglutinin or coagulant present in the filter pad can be reduced. Both FIGS. 6 and 7 are dose response plots of standardized whole blood samples including from 0 mg/dL to 400 mg/dL (milligram per deciliter) glucose and either 20% or 60% hematocrit (HCT). The test strips used in the assays plotted in FIG. 6 included a test pad incorporating the necessary reagents to assay for glucose, and a filter pad comprising a separating reagent composition including 0.225 mg/mL of the lectin from Solanum tuberosum (equivalent to 50 units/cm$^3$ of carrier matrix) and 0.3% by weight CREMOPHOR® EL incorporated into a WHATMAN PD107 glass fiber matrix. The test strips used in the assays plotted in FIG. 7 utilized a test pad incorporating the necessary reagents to assay for glucose, and a filter pad comprising a separating reagent composition including 0.045 mg/mL of the lectin from Solanum tuberosum (equivalent to 10 units/cm$^3$ of carrier matrix) and 1.3% by weight CREMOPHOR® EL incorporated into a WHATMAN PD107 glass fiber matrix. All the test strips included a transparent support strip to allow examination of the test pad for response to the glucose concentration of the test sample.

The test strips were used to assay standardized whole blood samples including 100, 200, 300 and 450 mg/dL glucose, and either 20% or 60% hematocrit. The test pads were examined instrumentally from the change in reflectance observed at 680 nm (nanometers). The reflectance, as taken from the reflectance scale of zero to one, was incorporated into the Kubelka-Munk function:

$$K/S=(1-R)^2/2R,$$

wherein K is the absorption coefficient, S is the scattering coefficient and R is reflectance. The calculated K/S value was plotted against the glucose concentration of the test sample. Generally, it can be stated that as reflectance decreases, the K/S value increases. The K/S value in turn is related to the reactivity of the test strip towards the predetermined constituent of interest. For example, FIGS. 6 and 7 show K/S values at 680 nm versus the glucose concentration of standardized blood samples. Each assay was run in duplicate, using two instruments. The graphed K/S values are the average K/S values for five replicate trials. The standard deviation over the replicate trials is approximately 0.1.

In particular, the plots in FIG. 6 show that the concentration of glucose in a whole blood sample including either 60% hematocrit or 20% hematocrit can be determined accurately by using the method and device of the present invention. The filter pad, including an agglutinin or a coagulant and a nonhemolytic surfactant, effectively separated the cellular components from the plasma or serum. The essentially identical plots of FIG. 6 demonstrate that no hematocrit dependence was observed. FIG. 6 shows that the dose response plots for assays on samples including 60% hematocrit and for assays on samples including 20% hematocrit are essentially identical over the entire range of glucose, both in regard to intercept and in regard to slope.

The plots in FIG. 7 also show that accurate assays of test samples, including 20% hematocrit or 60% hematocrit, for glucose can be performed by using a test strip including a filter pad having a separating reagent composition including only 0.05 mg/mL of the lectin from Solanum tuberosum incorporated therein. This amount of lectin is equivalent to 10 units of lectin per cubic centimeter (cm$^3$) of carrier matrix. It has been found that by increasing the amount of nonhemolytic surfactant in the filter pad, the amount of agglutinin or coagulant in the test pad can be reduced significantly. The dose response plots in FIG. 6 and in FIG. 7 show an essentially identical response to glucose over the range of 0 mg/mL to 500 mg/mL. However, the test strips used to generate the plots in FIG. 7, included only about one-fifth of the amount of agglutinin (0.045 mg/mL lectin compound to 0.225 mg/mL lectin) included in the test strips used to generate the plots in FIG. 6. Therefore, by increasing the amount of relatively-inexpensive nonhemolytic surfactant in the filter pad, the amount of relatively-expensive and difficult-to-produce agglutinin or coagulant in the filter pad was reduced by 80%

The reduced amount of agglutinin or coagulant in the filter pad did not adversely affect the assay results, regardless of the hematocrit value of the test sample, therefore providing a less expensive test strip that is independent of the hematocrit of the test sample and that provides more reproducible assay results. This result is illustrated in TABLE I showing that a device with a filter pad including a high amount of lectin (50 units per cm$^3$) and a low amount of nonhemolytic surfactant (0.3%), and a device with a filter pad including a low amount of lectin (10 units per cm$^3$) and a high amount of nonhemolytic surfactant (1.3%), have a similar hematocrit dependence, even though the amount of lectin was decreased by 80%.

TABLE I

TABLE I

| Hematocrit Bias in Glucose Assays for Test Samples Including 60% or 20% Hematocrit | | |
|---|---|---|
| Plasma Glucose (mg/dL) | Filter Pad | % Bias |
| 100 | A[1] | −2.3 |
|  | B[2] | 5.7 |
| 200 | A | −6.7 |
|  | B | −10.7 |
| 300 | A | −5.6 |
|  | B | −7.8 |
| 450 | A | 3.3 |
|  | B | 9.0 |

[1]Filter Pad A was immersed in a separating reagent composition including 0.045 mg/mL of the lectin from Solanum tuberosum and 1.3% by weight of the nonhemolytic surfactant CREMOPHOR ® EL; and
[2]Filter Pad B was immersed in a separating reagent composition including 0.225 mg/mL of the lectin from Solanum tuberosum and 0.3% by weight of the nonhemolytic surfactant CREMOPHOR ® EL.

The linear dose response plots presented in FIG. 6 and 7 demonstrate the accuracy of the assay procedure for glucose, and especially demonstrate that the filter pad of the test device effectively eliminated the interferences attributed to the cellular components of the whole blood samples while allowing the predetermined constituent of interest to chromatograph through the filter pad to saturate the test pad. The dose response plots also demonstrate that the test device and method of the present invention permit the effective removal of assay interferents followed by fast, safe, economical and accurate detection of the assay response by currently available instrumental, or alternatively visual, detection techniques.

To demonstrate that nonhemolytic surfactants other than CREMOPHOR® EL can be included in a carrier matrix to assist a lectin, thrombin or thrombin-like compound separate the cellular components from a test sample, the nonhemolytic anionic surfactant CRODAFOS SG, or the nonhemolytic nonionic surfactant TRITON X-405, at 1.3% by weight, was included in a separating reagent composition that further included 0.045 mg/mL of the lectin from Solanum tuberosum. The carrier matrix was a glass fiber matrix, and filter pads comprising the glass fiber matrix and the separating reagent composition were used in test strips to assay for glucose. The test samples were standardized and included either 0, 100, 150, 350 or 500 mg/dL of glucose and either 20%, 40% or 60% hematocrit (HCT).

Figure 8:
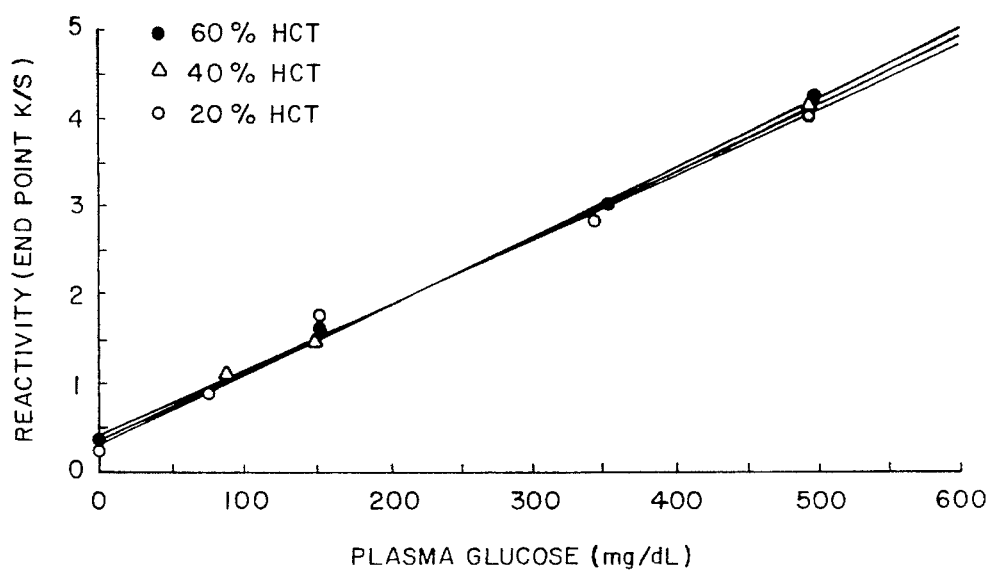
Figure 9:
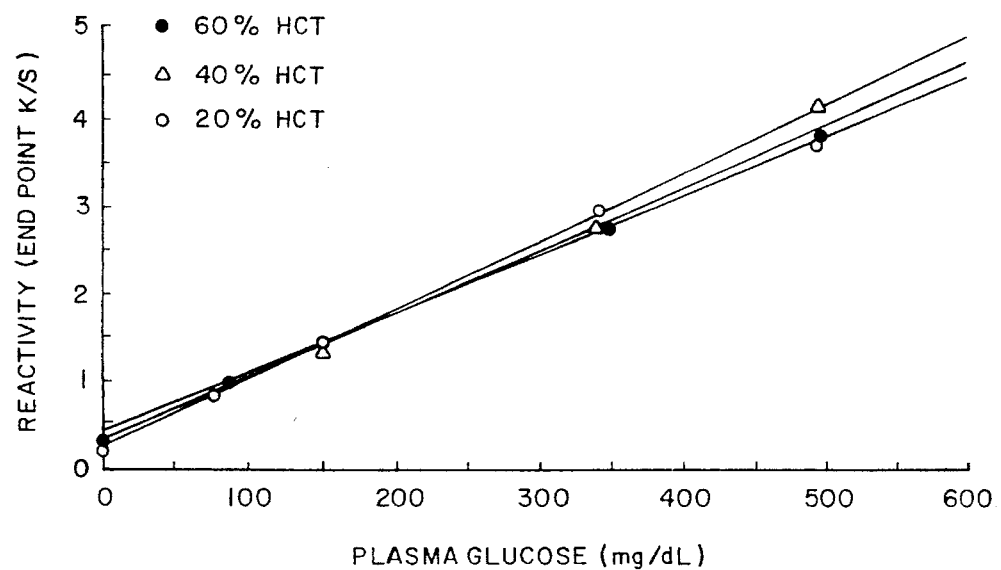

FIGS. 8 and 9 are dose response plots of assays for glucose derived from a change in reflectance at 680 nm, as described above. The plots in FIGS. 8 and 9 show that accurate assays for glucose can be performed on test samples including from 20% to 60% hematocrit when the anionic nonhemolytic surfactant CRODAFOS SG or the nonionic nonhemolytic surfactant TRITON X-405 is utilized as the nonhemolytic surfactant in the presence of a low amount (0.045 mg/mL) of lectin. The plots of FIGS. 8 and 9 illustrate that the assay is independent of hematocrit, and is accurate. It also should be noted that in separate experiment an anionic surfactant that was not ethoxylated or propoxylated, i.e., sodium alpha-olefin sulfonate, at about 0.1% by weight, was incorporated into the carrier matrix of the filter pad in addition to the agglutinin or coagulant. It was observed that the wetting of the carrier matrix was improved, therefore reducing the time for plasma or serum separation. However, the presence of such a low amount of nonethoxylated or nonpropoxylated anionic surfactant in the filter pad did not significantly increase the amount of cellular components separated from the whole blood sample.

In accordance with another important feature of the present invention, the filter pad of the test device effectively separated the cellular components of whole blood from the plasma or serum even in the presence of anticoagulants, provided that the filter pad includes a lectin, a thrombin, a thrombin-like compound or a combination thereof and a nonhemolytic surfactant. Specifically, whole blood containing anticoagulants, such a heparin or ethylenediaminetetraacetic acid (EDTA), is amenable to the separation and testing method and the device of the present invention. Therefore, fresh blood samples can be treated with an anticoagulant, then assayed for a predetermined constituent by the process and device of the present invention at a later date. In accordance with another important feature of the present invention, hemolysis is essentially eliminated in separations utilizing lectins and nonhemolytic surfactant, and was minimal in separations utilizing a thrombin or a thrombin-like compound and a nonhemolytic surfactant. In every case however, the degree of lysis was sufficiently low such that the coloration from the highly-colored red blood cells did not materially interfere in any subsequent assays for a plasma- or serum-soluble constituent.

In addition to an unexpectedly efficient separation of the red blood cells from the plasma or serum, the process and device of the present invention allow a sufficiently large and assayable amount of plasma or serum to reach the test pad of the test device. Furthermore, the plasma or serum reaches the test pad of the test device in an essentially unaltered form. Generally, the proper amount of serum or plasma has reached the test pad when the test pad is saturated with plasma or serum. This is accomplished either by using a sufficiently large whole blood sample to assure plasma or serum saturation of the test pad, or, preferably, by adjusting the relative sizes of the filter pad and the test pad such that the test pad is saturated with plasma or serum. Generally, the size of the filter pad is directly related to the predetermined blood sample size and the separating reagent composition utilized. A precisely-measured whole blood sample volume is not necessary. This process allows for an essentially fixed amount of plasma or serum to reach the test pad, and renders a more accurate soluble constituent determination. The variables of blood sample size, filter pad size, test pad size and the amount of indicator reagent composition impregnated into the test area easily can be determined by those skilled in the art after the particular nonhemolytic surfactant, and agglutinin, coagulant or combination thereof are selected for the separating reagent composition to be incorporated into the filter pad.

In accordance with another important feature of the present invention, essentially none of the plasma- or serum-soluble constituents of the whole blood sample is separated from the plasma or serum with the cellular components, nor do intercellular components of the cells contaminate the separated plasma or serum. Surprisingly, the method and device of the present invention separated the plasma or serum from the cellular components with no observable increase in, or loss of, plasma- or serum-soluble constituents, and with essentially no evidence of red blood cells. In contrast, the salts used in the method of Fretter, U.S. Pat. No. 3,552,925, tend to precipitate the high molecular weight constituents of plasma or serum, such as cholesterol, therefore making such constituents unavailable for assay at the test pad of the test device. However, the separating reagent composition of the present invention does not promote precipitation of high molecular weight plasma or serum constituents.

Thrombins and thrombin-like compounds promoted sufficient lysis to block the assay of cholesterol in serum, but lysis can be controlled by using normal saline. Hemolysis inhibiting agents also can be incorporated into the carrier matrix of the filter pad of the present invention. Therefore, high molecular weight components of plasma or serum can be assayed by using the separating reagent composition of the present invention, including a nonhemolytic surfactant and a coagulant or an agglutinin. Also, in certain instances, hemolysis, or blood staining, is desirable because assays then can be performed on the constituents present within the red blood cells.

In addition to the fast and efficient separation of the serum or plasma from the cellular components of whole blood, and the essentially unimpeded migration of unaltered plasma or serum to the test pad, the method and device of the present invention allow a quantitative assay of a plasma- or serum-soluble constituent without dilution of the whole blood or plasma and without interference from the highly-colored red blood cells. Testing the undiluted serum or plasma both omits a manipulative step and, more importantly, eliminates the possibility of technician error and technician contact with the potentially-infectious test sample.

A suitable chromogenic indicator reagent composition is incorporated into the test pad in a sufficient amount to allow a detectable interaction with the freshly separated and undiluted plasma or serum. The extent of the chromogenic reaction, and therefore the quantitative amount of the predetermined soluble constituent, then is determined by chromogenic detection techniques, either visual or instrumental, that are well-known in the art. Accordingly, the method and test device demonstrate appreciable advantages over the prior art methods and devices because the test strip is more economical and produces more reproducible results; the assay is independent of the hematocrit value of the test sample; the technician is not required to wipe the separated cellular components from the device, thereby avoiding a manipulative step and a potential technician error; and the technician avoids physical contact with the blood sample.

Therefore, an accurate and reliable assay of a small volume of whole blood for a predetermined soluble plasma constituent is achieved within about 2 minutes and usually within one minute, without interference by the cellular components of the whole blood. The assay is simple, economical and safe because additional manipulative steps, like wiping or rinsing of the test device, or like centrifuging, are unnecessary. Furthermore, the device and method are safe because the technician is effectively protected from inadvertent contact with the potentially-infectious whole blood sample. The entire whole blood sample, both the cellular components in the filter pad and the plasma or serum in the test pad, is retained by the elements of the test device. Therefore, after discarding the test device, human contact with the test device is essentially precluded. Such a feature is new in the art, wherein prior art methods and devices for testing serum or plasma led to the possibility of human contact with the blood sample, either in the wiping or rinsing of the cellular material from the test device or in blood transfers and dilutions in centrifuging and related physical separation methods.

Examples 2 through 4 more fully and specifically demonstrate assays performed in accordance with the method and test device of the present invention for a predetermined soluble plasma or serum constituent.

EXAMPLE 2

DETERMINATION OF TOTAL BILIRUBIN IN PLASMA OR SERUM

An undiluted whole blood sample is assayed for total bilirubin by a test device as illustrated in FIG. 3. The test device contacts a whole blood sample, such as a pinprick amount, at the sample port of the device, and the whole blood sample is absorbed by a filter pad comprising a carrier matrix incorporating a separating reagent composition including a lectin and a nonionic nonhemolytic surfactant. The blood sample chromatographs through the impregnated filter pad, whereby the cellular components of the whole blood are separated from the plasma or serum. The blood sample is of sufficient size such that after chromatographing through the filter pad, the amount of serum or plasma in the sample is sufficient to completely wet, or saturate, a test pad that is in releasable contact with the filter pad. After saturation of the test pad by the plasma or serum, the filter pad, contaminated with the cellular components of the whole sample, is detached from the test device by peeling, tearing or snapping off the portion of the test device handle secured to the filter pad. The filter pad is detached from the test pad to expose the test pad for examination of a response, i.e., the chromogenic change, to the total bilirubin content in the serum or plasma. An indicator reagent composition comprising 0.4% w/w 2,4-dichloroaniline, 1.1% w/w sodium nitrite, 57.2% w/w diphylline, 35.5% w/w buffer, and 5.8% w/w nonreactive ingredients, and previously incorporated into the test pad of the test device, interacts with the bilirubin in the serum or plasma to produce a measurable chromogenic change that correlates quantitatively to the total bilirubin content in the serum of plasma.

The chromogenic change in the test pad is determined visually, such as by a comparison to a standardized color chart, or, alternatively, instrumentally, such as by a reflectance measuring instrument. When using a reflectance photometer, the method provides a response to the concentration of total bilirubin in an undiluted serum of plasma sample without interference from the cellular components of the whole blood sample. Furthermore, the assay is independent of the hematocrit value of the whole blood sample. The assay method is based on the van den Bergh reaction, modified to use 2,4-dichloroaniline and a diazo coupling accelerator. The final product, azobilirubin, behaves as an indicator that is red-purple in color under acid conditions. The concentration of total bilirubin in a sample is quantified from a calibration curve.

A calibration curve is generated internally. Once the calibration curve is generated, each assay required approximately 60 μL (microliter) of whole blood and one device of the present invention. After an incubation period of about 75 seconds, the concentration of total bilirubin in the test sample is determined by measuring the change in reflectance at 560 nanometers (nm) with reference to a calibration curve generated using calibrators. Preferably, the filter pad is separated from the test pad prior to the 75 second incubation period to preclude inadvertent contamination of the plasma or serum by the cellular components of the test sample. Results are obtained in mg/dL or μmol/l directly from a reflectance photometer. No calculations are required. The test responds to from 0.4 mg/dL to 7.5 mg/dL (7 μmol/l to 130 μmol/l) serum or plasma total bilirubin. Serum total bilirubin values of 0.1 mg/dL to 1.2 mg/dL (1.7 μmol/l to 20.5 μmol/l) have been suggested as the adult normal range.

EXAMPLE 3

DETERMINATION OF CREATININE IN PLASMA OR SERUM

The identical method described in Example 2 is used to quantitatively determine the amount of creatinine in an undiluted whole blood sample with a test device illustrated in FIG. 2. However, the indicator reagent composition used in the creatinine assay comprises 43.5% w/w potassium hydroxide, 55.8% w/w 3,5-dinitrobenzoic acid, and 0.6% w/w nonreactive ingredients.

When used with a reflectance photometer, the method provides a direct reading of the concentration of creatinine in the test sample. The assay method is based on the Benedict-Behre reaction wherein creatinine interacts with 3,5-dinitrobenzoic acid in an alkaline medium to form a purple-colored complex. The concentration of creatinine in the sample is quantified from a calibration curve generated using calibrators.

During an incubation and test period of about 30 seconds, the concentration of creatinine in the sample is determined by measuring the rate of change in reflectance at 560 nm with reference to a calibration curve generated using calibrators. The result is displayed digitally by a reflectance photometer.

A calibration curve is generated internally. Once the calibration curve is generated, each assay requires approximately 60 μL of whole blood sample and one device of the present invention. By using a reflectance photometer, no calculations are required. The test covers a range of 0 mg/dL to 15 mg/dL (0 μmol/l to 1326 μmol/l) serum or plasma creatinine. Serum creatinine values of 0.6 mg/dL to 1.2 mg/dL (53 μmol/l to 106 μmol/l) for males and 0.5 to 1.0 mg/dL (44 to 88 μmol/l) for females have been suggested as the adult normal range. Nevertheless, the range afforded is sufficiently large to test populations having a creatinine concentration several times higher than the normal suggested range.

EXAMPLE 4

DETERMINATION OF CHOLESTEROL IN PLASMA OR SERUM

Undiluted whole blood samples, including a standardized amount of cholesterol, are assayed for cholesterol content by using test devices as illustrated in FIG. 3. Each test device includes a test pad comprising a substrate material of either a polyamide, such as nylon, like BIODYNE B, having a 3μ(micron) pore size and available from Pall Corporation, or a polyvinylidene fluoride, like DURAPORE, having a 0.65μ pore size, available from Millipore Corporation, Bedford, Mass. The substrate material of the test pad incorporates an indicator reagent composition first by immersing the substrate material into an aqueous solution including about 1.5% (w/w) tetramethylbenzidine hydrochloride indicator dye, and about 0.4% (w/w) poly(methyl vinyl ether/maleic anhydride) (GANTREZ AN-139, available from GAF Chemicals Corp., Wayne, N.J.). The impregnated substrate material then is dried in a hot air convection oven at about 50° C. for from about 5 minutes to about 10 minutes. The impregnated substrate material then is immersed in a second aqueous solution including:

| | |
|---|---|
| 0.2M Phosphate Buffer (pH 6.0) | 66.6% (w/w) |
| Tetramethyldecynediol ethoxylated with 30 moles ethylene oxide- (SURFYNOL 485, available from Air Products and Chemicals, Inc., Allentown, Pa.) | 1.3% (w/w) |
| Glycerol | 6.4% (w/w) |
| Sodium taurocholate | 0.7% (w/w) |
| Peroxidase | 500 U/mL |
| Cholesterol Esterase | 500 U/mL |
| Cholesterol Oxidase | 250 U/mL |
| Polyvinylpyrrolidone (PVP K-60 available from GAF Chemicals Corp., Wayne, NJ) (45% w/w) | 23.8% (w/w) |

After the second impregnation, the substrate material again is dried in a hot air convention oven at about 50° C. for from about 5 minutes to about 10 minutes to provide a test pad to determine the amount of cholesterol in a liquid test sample.

Each test device also includes a filter pad comprising a carrier matrix incorporated a separating reagent composition including a nonhemolytic surfactant and a lectin. The carrier matrix, a glass fiber matrix, having a pore size of from about 1μ to about 6μ, and available from Whatman Ltd. or Millipore Corporation, is immersed into an aqueous separating reagent composition including about 0.05% (w/w) of the lectin from Phytolacca americana and about 0.05% (w/w) of an ethoxylated oxide (TRITON X-45, available from Rohm and Haas Co., Philadelphia, Pa.). After incorporating the separating reagent composition into the glass fiber matrix, the impregnated glass fiber matrix is scraped with a glass rod to remove any excess separating reagent composition. The impregnated glass fiber matrix then is dried in a hot air convection oven at about 50° C. for about 30 minutes to provide a filter pad of the present invention.

The test pad and the filter pad then are positioned on a test device as illustrated in FIG. 3 to assay whole blood samples for cholesterol. Each assay requires approximately 60 μl of whole blood sample and one test device of the present invention.

The assays are performed by first making a small puncture in any part of the body. The sample port of the test device then contacts whole blood seeping from the puncture. When the sample port of the test device is filled, the test device is removed form the puncture area. It is observed that the whole blood sample is absorbed sufficiently into the filter pad such that excess whole blood sample does not remain in a pool on the sample port or on any outside surface of the test device. After a sufficient time, such as about 1 minute, the filter pad is separated from the test device and discarded. After allowing approximately 1 to 2 additional minutes for generation of a complete response, the exposed test pad then is examined instrumentally in a reflectance measuring instrument, i.e., a GLUCOMETER reflectance photometer instrument, available from Miles, Inc., Elkhart, Ind. Alternatively, the exposed test pad is examined visually, such as by visually comparing the test pad to a standardized color chart. After examining the test pad for a response, the test pad is discarded. The method and test device preclude the technician from contacting any surface containing the potentially-infectious whole blood sample.

The color transition resulting from an interaction between the cholesterol-containing serum or plasma of the whole blood sample with the indicator reagent composition incorporated into the test pad is examined by reflectance photometry. In general, comparison of the color transition resulting from contacting a test pad with a blood sample of unknown cholesterol concentration gives a quantitative assay for the cholesterol concentration in the blood sample. Then, a dose response plot is graphed to demonstrate that the intensity of the color transition of the assay varied in direct proportion to the cholesterol concentration of the test sample.

With the appropriate chemistry, assays on undiluted plasma or serum, utilizing known chromogenic reactions and a reflectance spectrophotometer, also can be performed for uric acid, potassium ion, glucose, galactose, urea, phenylalanine, triglycerides, various enzymes and other soluble constituents of whole blood or other biological samples. See, for example, U.K. Patent No. 2,014,155; U.S. Pat. No. 4,186,251; U.S. Pat. No. 4,057,394; and related patents, hereby incorporated by reference.

It will be understood that the present disclosure has been made only by way of preferred embodiment and that numerous changes in details of construction, combination, and arrangement of parts can be resorted to without departing from the spirit and scope of the invention as hereunder claimed.

What is claimed is:

1. A device for separating undiluted plasma or serum from an undiluted whole blood sample including a filter pad consisting essentially of a single carrier matrix having homogeneously incorporated therein from about 5 to about 50 units of a blood cell agglutinizing agent per $cm^3$ of the carrier matrix, or from about 40 to about 100 NIH units of a blood cell coagulating agent per $cm^3$ of the carrier matrix, or a mixture thereof, and from about 0.3% to about 1.5% by weight of the carrier matrix of a nonhemolytic surfactant, to agglutinate or coagulate the cellular components from the undiluted whole blood sample in the area of the carrier matrix while allowing a quantity of the undiluted plasma or serum portion of the undiluted whole blood sample to chromatographically flow completely through the carrier matrix separate from the cellular components of the blood, wherein the agglutinizing agent is a lectin, the coagulating agent is a thrombin compound and the nonhemolytic surfactant is selected from the group consisting of octoxynol 40, PEG-36 castor oil, $C_{11-15}$ pareth-12, $C_{12-15}$ pareth-9, ceteareth-27, ceteth-30, laureth-23, oleth-15, PEG-20 laurate, PEG-36 oleate, PEG-44 sorbitan laurate, PEG-30 stearate, steareth-27, PEG-11 cocamide, PEG-15 cocamine, PEG-15 tallow amine, PEG-20 hydrogenated castor oil, PPG-5-ceteth 20, PPG-myreth-11, steareth-10, trideceth-15, $C_{11-15}$ pareth-7 carboxylic acid, $C_{12-13}$ pareth-5 carboxylic acid, $C_{12-15}$ pareth-7 carboxylic acid, ceteareth-25 carboxylic acid, deceth-7 carboxylic acid, isosteareth-6 carboxylic acid, isosteareth-11 carboxylic acid, coceth-7 carboxylic acid, laureth-5 carboxylic acid, laureth-10 carboxylic acid, trideceth-4 carboxylic acid, trideceth-7 carboxylic acid, trideceth-15 carboxylic acid, trideceth-19 carboxylic acid, $C_{12-15}$ pareth-2 phosphate, ceteareth-4 phosphate, deceth-4 phosphate, dilaureth-10 phosphate, dioleth-8 phosphate, laneth-4 phosphate, laureth-3 phosphate, laureth-8 phosphate, nonoxynol-6 phosphate, nonoxynol-9 phosphate, nonoxynol-10 phosphate, nonyl nonoxynol-7 phosphate, nonyl nonoxynol-9 phosphate, nonyl nonoxynol-10 phosphate, nonyl nonoxynol-15 phosphate, nonyl nonoxynol-24 phosphate, oleth-3 phosphate, oleth-4 phosphate, oleth-10 phosphate, oleth-20 phosphate, potassium octoxynol-12 phosphate, PPG-5-ceteth phosphate, PPG- 10 cetyl ether phosphate, triceteareth-4 phosphate, triceteth-5 phosphate, trideceth-6 phosphate, trilaneth-4 phosphate, trilaureth-4 phosphate, trioleth-8 phosphate, and combinations thereof, wherein the amount of agglutinin or coagulant incorporated in the carrier matrix is about two to about five times less than the amount of agglutinin or coagulant used in the absence of a nonhemolytic surfactant.

2. An analyte test device that separates cellular and particulate components from a liquid test sample and that determines the presence or concentration of a soluble component of the liquid test sample consisting essentially of:

a support strip;

a test pad secured to the support strip, the test pad comprising a substrate material incorporating an indicator reagent composition that undergoes a detectable change in response to the soluble component of the liquid test sample when in contact with the liquid test sample; and a filter pad of sufficient size to separate the cellular and particulate components from the liquid test sample, the filter pad consisting essentially of a single carrier matrix having homogeneously incorporated therein from about 5 to about 50 units of an agglutinin per $cm^3$ of the carrier matrix or from about 40 to about 100 NIH units of a coagulant per $cm^3$ of the carrier matrix, or a mixture thereof, and from about 0.3% to about 1.5% by weight of the carrier matrix of a nonhemolytic surfactant selected from the group consisting of octoxynol 40, PEG-36 castor oil, $C_{11-15}$ pareth-12, $C_{12-15}$ pareth-9, ceteareth-27, ceteth-30, laureth-23, oleth-15, PEG-20 laurate, PEG-36 oleate, PEG-44 sorbitan laurate, PEG-30 stearate, steareth-27, PEG-11 cocamide, PEG-15 cocamine, PEG-15 tallow amine, PEG-20 hydrogenated castor oil, PPG-5-ceteth 20, PPG-myreth-11, steareth-10, trideceth-15, $C_{11-15}$ pareth-7 carboxylic acid, $C_{12-13}$ pareth-5 carboxylic acid, $C_{12-15}$ pareth-7 carboxylic acid, ceteareth-25 carboxylic acid, deceth-7 carboxylic acid, isosteareth-6 carboxylic acid, isosteareth-11 carboxylic acid, coceth-7 carboxylic acid, laureth-5 carboxylic acid, laureth-10 carboxylic acid, trideceth-4 carboxylic acid, trideceth-7 carboxylic acid, trideceth-15 carboxylic acid, trideceth-19 carboxylic acid, $C_{12-15}$ pareth-2 phosphate, ceteareth-4 phosphate, deceth-4 phosphate, dilaureth-10 phosphate, dioleth-8 phosphate, laneth-4 phosphate, laureth-3 phosphate, laureth-8 phosphate, nonoxynol-6 phosphate, nonoxynol-9 phosphate, nonoxynol-10 phosphate, nonyl nonoxynol-7 phosphate, nonyl nonoxynol-9 phosphate, nonyl nonoxynol-10 phosphate, nonyl nonoxynol-15 phosphate, nonyl nonoxynol-24 phosphate, oleth-3 phosphate, oleth-4 phosphate, oleth-10 phosphate, oleth-20 phosphate, potassium octoxynol-12 phosphate, PPG-5-ceteth phosphate, PPG-10 cetyl ether phosphate, triceteareth-4 phosphate, triceteth-5 phosphate, trideceth-6 phosphate, trilaneth-4 phosphate, trilaureth-4 phosphate, trioleth-8 phosphate, and combinations thereof;

wherein the filter pad is positioned such that the liquid test sample first contacts the filter pad to chromatographically flow through the filter pad to contact the test pad, and wherein the amount of agglutinin or coagulant incorporated in the carrier matrix is about two to about five times less than the amount of agglutinin or coagulant used in the absence of a nonhemolytic surfactant.

3. The analyte test device of claim 2 wherein the carrier matrix is filter paper; and wherein the agglutinin is a lectin from Solanum tuberosum, the coagulant is bovine thrombin and the nonhemolytic surfactant is selected from the group consisting of octoxynol 40, PEG-36 castor oil, PPG-5-ceteth-10 phosphate, and combinations thereof.

4. The analyte test device of claim 2 wherein the liquid test sample is a biological sample.

5. The analyte test device of claim 4 wherein the biological sample is whole blood.

6. The analyte test device of claim 5 wherein the indicator reagent composition undergoes a chromogenic change that is independent of an amount of hematocrit in the whole blood, and wherein the test pad is examined for the chromogenic change visually or by instrument.

7. The analyte test device of claim 2 wherein the carrier matrix of the filter pad is selected from the group consisting of silica gel, alumina, diatomaceous earth, filter paper, chromatographic paper, glass fiber, cellulose acetate, polyvinyl chloride, polyacrylamide, polyacrylate, polyurethane, crosslinked dextran, polyethylene, polypropylene, polyvinylidene fluoride, polysulfone, and combinations thereof.

8. The analyte test device of claim 2 wherein the agglutinin is a lectin selected from the group consisting of *Abrus precatorius* (abrin, Jequirty bean), *Agaricus bisporus* (mushroom), *Bauhinia purpurea* (camels foot tree), *Caragana arborescens* (Siberian pea tree), *Cicer arietinum* (chick pea), *Codium fragile* (Green marine algae), *Canavalia ensiformis* (Con A, Concanavalin A, Jack bean), *Datura stramonium* (jimson weed), *Glycine max* (Soybean), *Lathyrus odoratus* (Sweet Pea), *Lens culinaris* (Lentil), *Limulus polyphemus* (Horseshoe crab, limulin), *Lycopersicon esculentum* (Tomato), *Maclura pomifera* (Osage orange), *Mycoplasma gallisepticum, Naja mocambique mocambique* (cobra venom), *Naja naja kaouthia* (cobra venom), *Perseau americana* (Avocado), *Phaseolus coccineus* (Scarlet runner bean), *Phaseolus vulgaris* (Red Kidney bean), *Phytolacca americana* (Pokeweed), *Pisum sativum* (garden pea), *Pseudomonas aeruginosa, Psophocarpus tetragonolobus* (winged bean), *Ricinus communis* (Castor bean), *Robinia pseudoacacia* (black locust, false acacia), *Sambucus nigra* (elder), *Solanum tuberosum* (Potato), *Triticum vulgaris* (Wheat germ), *Vicia faba* (fava bean, broad bean), *Vicia sativa, Vigna radiata* (Mung bean), *Viscum album* (European mistletoe), *Wisteria floribunda* (Japanese wisteria), and combinations thereof.

9. The analyte test device of claim 2 wherein the coagulant is a thrombin compound.

10. The analyte test device of claim 9 wherein the thrombin compound is selected from the group consisting of bovine thrombin, human thrombin, horse thrombin, goat thrombin, mouse thrombin, rat thrombin, pig thrombin, sheep thrombin and combinations thereof.

11. The analyte test device of claim 9 wherein the thrombin compound is selected from the group consisting of acutase, agkistrodon contortrix, ancrod, atroxin, crotalase and combinations thereof.

12. A method of manufacturing a filter pad for separating cellular components from a whole blood sample said method comprising the steps of:

a) forming a solution of a separating reagent composition, said separating reagent composition comprising:
  i) from about 4 to about 4000 units of an agglutinin, or from about 90 to about 900 NIH units of a coagulant, or a combination thereof,
  ii) from about 0.05% to about 3% by weight of a nonhemolytic surfactant, and
  iii) an aqueous carrier;

b) applying the separating reagent composition solution to a single carrier matrix; and c) removing a sufficient amount of the aqueous carrier from the separating reagent composition solution applied to the carrier matrix to dry the carrier matrix, and provide the filter pad comprising the single carrier matrix having homogeneously incorporated therein from about 5 to about 50 units of the agglutinin per cm$^3$ of the carrier matrix or from about 40 to about 100 NIH units of the coagulant per cm$^3$ of the carrier matrix, or a combination thereof; and from about 0.3% to about 1.5% by weight of the carrier matrix of the nonhemolytic surfactant, wherein the nonhemolytic surfactant is selected from the group consisting of octoxynol 40, PEG-36 castor oil, $C_{11-15}$ pareth-12, $C_{12-15}$ pareth-9, ceteareth-27, ceteth-30, laureth-23, oleth-15, PEG-20 laurate, PEG-36 oleate, PEG-44 sorbitan laurate, PEG-30 stearate, steareth-27, PEG-11 cocamide, PEG-15 cocamine, PEG-15 tallow amine, PEG-20 hydrogenated castor oil, PPG-5-ceteth 20, PPG-myreth-11, steareth-10, trideceth-15, $C_{11-15}$ pareth-7 carboxylic acid, $C_{12-13}$ pareth-5 carboxylic acid, $C_{12-15}$ pareth-7 carboxylic acid, ceteareth-25 carboxylic acid, deceth-7 carboxylic acid, isosteareth-6 carboxylic acid, isosteareth-11 carboxylic acid, coceth-7 carboxylic acid, laureth-5 carboxylic acid, laureth-10 carboxylic acid, trideceth-4 carboxylic acid, trideceth-7 carboxylic acid, trideceth-15 carboxylic acid, trideceth-19 carboxylic acid, $C_{12-15}$ pareth-2 phosphate, ceteareth-4 phosphate, deceth-4 phosphate, dilaureth-10 phosphate, dioleth-8 phosphate, laneth-4 phosphate, laureth-3 phosphate, laureth-8 phosphate, nonoxynol-6 phosphate, nonoxynol-9 phosphate, nonoxynol-10 phosphate, nonyl nonoxynol-7 phosphate, nonyl nonoxynol-9 phosphate, nonyl nonoxynol-10 phosphate, nonyl nonoxynol-15 phosphate, nonyl nonoxynol-24 phosphate, oleth-3 phosphate, oleth-4 phosphate, oleth-10 phosphate, oleth-20 phosphate, potassium octoxynol-12 phosphate, PPG-5-ceteth phosphate, PPG-10 cetyl ether phosphate, triceteareth-4 phosphate, triceteth-5 phosphate, trideceth-6 phosphate, trilaneth-4 phosphate, trilaureth-4 phosphate, trioleth-8 phosphate, and combinations thereof, wherein the amount of agglutinin or coagulant incorporated in the carrier matrix is about two to about five times less than the amount of agglutinin or coagulant used in the absence of a nonhemolytic surfactant.

13. An analyte test device that separates undiluted plasma or serum from an undiluted whole blood sample and that determines the presence or concentration of a soluble component of the undiluted plasma or serum, said test device consisting essentially of:

a support strip;

a test pad secured to the support strip, the test pad comprising a substrate material incorporating an indicator reagent composition that undergoes a detectable change in response to the soluble component of the undiluted plasma or serum when in contact with the undiluted plasma or serum; and a filter pad of sufficient size to separate cellular and particulate components of the undiluted whole blood sample from the undiluted plasma or serum, the filter pad consisting essentially of a single carrier matrix having homogeneously incorporated therein from about 5 to about 50 units of an agglutinin per cm$^3$ of the carrier matrix, and from about 0.3% to about 1.5% by weight of the carrier matrix of a nonhemolytic surfactant selected from the group consisting of octoxynol 40, PEG-36 castor oil, $C_{11-15}$ pareth-12, $C_{12-15}$ pareth-9, ceteareth-27, ceteth-30, laureth-23, oleth-15, PEG-20 laurate, PEG-36 oleate, PEG-44 sorbitan laurate, PEG-30 stearate, steareth-27, PEG-11 cocamide, PEG-15 cocamine, PEG-15 tallow amine, PEG-20 hydrogenated castor oil, PPG-5-ceteth 20, PPG-myreth-11, steareth-10, trideceth-15, $C_{11-15}$ pareth-7 carboxylic acid, $C_{12-13}$ pareth-5 carboxylic acid, $C_{12-15}$ pareth-7 carboxylic acid, ceteareth-25 carboxylic acid, deceth-7 carboxylic acid, isosteareth-6 carboxylic acid, isosteareth-11 carboxylic acid, coceth-7 carboxylic acid, laureth-5 carboxylic acid, laureth-10 carboxylic acid, trideceth-4 carboxylic acid, trideceth-7 carboxylic acid, trideceth-15 carboxylic acid, trideceth-19 carboxylic acid, $C_{12-15}$ pareth-2 phosphate, ceteareth-4 phosphate, deceth-4 phosphate, dilaureth-10 phosphate, dioleth-8 phosphate, laneth-4 phosphate, laureth-3 phosphate, laureth-8 phosphate, nonoxynol-6 phosphate, nonoxynol-9 phosphate, nonoxynol-10 phosphate, nonyl nonoxynol-7 phosphate, nonyl nonoxynol-9 phosphate, nonyl nonoxynol-10 phosphate, nonyl nonoxynol-15 phosphate, nonyl nonoxynol-24 phosphate, oleth-3 phosphate, oleth-4 phosphate, oleth-10 phosphate, oleth-20 phosphate, potassium octoxynol-12 phosphate, PPG-5-ceteth phosphate, PPG-10 cetyl ether phosphate, triceteareth-4 phosphate, triceteth-5 phosphate, trideceth-6 phosphate, trilaneth-4 phosphate, trilaureth-4 phosphate, trioleth-8 phosphate, and combinations thereof;

wherein the filter pad is positioned such that the undiluted whole blood sample first contacts the filter pad to chromatographically flow through the filter pad to contact the test pad, and wherein the amount of agglutinin or coagulant incorporated in the carrier matrix is about two to about five times less than the amount of agglutinin or coagulant used in the absence of a nonhemolytic surfactant.

14. The analyte test device of claim 13 wherein the carrier matrix of the filter pad is filter paper.

15. The analyte test device of claim 13 wherein the nonhemolytic surfactant is selected from the group consisting of PEG-36 castor oil, PPG-5-ceteth-10 phosphate, and combinations thereof.

16. An analyte test device that separates undiluted plasma or serum from an undiluted whole blood sample and that determines the presence or concentration of a soluble component of the undiluted plasma or serum, said test device consisting essentially of:

a support strip;

a test pad secured to the support strip, the test pad comprising a substrate material incorporating an indicator reagent composition that undergoes a detectable change in response to the soluble component of the undiluted whole blood sample when in contact with the undiluted plasma or serum; and a filter pad of sufficient size to separate the cellular and particulate components of the undiluted whole blood sample from the undiluted plasma or serum, the filter pad consisting essentially of a single carrier matrix having homogeneously incorporated therein from about 40 to about 100 NIH units of a coagulant per cm$^3$ of the carrier matrix, or a mixture thereof, and from about 0.3% to about 1.5% by weight of the carrier matrix of a nonhemolytic surfactant is selected from the group consisting of octoxynol 40, PEG-36 castor oil, $C_{11-15}$ pareth-12, $C_{12-15}$ pareth-9, ceteareth-27, ceteth-30, laureth-23, oleth-15, PEG-20 laurate, PEG-36 oleate, PEG-44 sorbitan laurate, PEG-30 stearate, steareth-27, PEG-11 cocamide, PEG-15 cocamine, PEG-15 tallow amine, PEG-20 hydrogenated castor oil, PPG-5-ceteth 20, PPG-myreth-11, steareth-10, trideceth-15, $C_{11-15}$ pareth-7 carboxylic acid, $C_{12-13}$ pareth-5 carboxylic acid, $C_{12-15}$ pareth-7 carboxylic acid, ceteareth-25 carboxylic acid, deceth-7 carboxylic acid, isosteareth-6 carboxylic acid, isosteareth-11 carboxylic acid, coceth-7 carboxylic acid, laureth-5 carboxylic acid, laureth-10 carboxylic acid, trideceth-4 carboxylic acid, trideceth-7 carboxylic acid, trideceth-15 carboxylic acid, trideceth-19 carboxylic acid, $C_{12-15}$ pareth-2 phosphate, ceteareth-4 phosphate, deceth-4 phosphate, dilaureth-10 phosphate, dioleth-8 phosphate, laneth-4 phosphate, laureth-3 phosphate, laureth-8 phosphate, nonoxynol-6 phosphate, nonoxynol-9 phosphate, nonoxynol-10 phosphate, nonyl nonoxynol-7 phosphate, nonyl nonoxynol-9 phosphate, nonyl nonoxynol-10 phosphate, nonyl nonoxynol-15 phosphate, nonyl nonoxynol-24 phosphate, oleth-3 phosphate, oleth-4 phosphate, oleth-10 phosphate, oleth-20 phosphate, potassium octoxynol-12 phosphate, PPG-5-ceteth phosphate, PPG-10 cetyl ether phosphate, tricetheareth-4 phosphate, triceteth-5 phosphate, trideceth-6 phosphate, trilaneth-4 phosphate, trilaureth-4 phosphate, trioleth-8 phosphate, and combinations thereof;

wherein the filter pad is positioned such that the undiluted whole blood sample first contacts the filter pad to chromatographically flow through the filter pad to contact the test pad, and wherein the amount of agglutinin or coagulant incorporated in the carrier matrix is about two to about five times less than the amount of agglutinin or coagulant used in the absence of a nonhemolytic surfactant.

* * * * *